United States Patent
Wan et al.

(10) Patent No.: US 12,012,456 B2
(45) Date of Patent: Jun. 18, 2024

(54) ANTI-INTERLEUKIN-4 RECEPTOR (IL-4R) SINGLE-DOMAIN ANTIBODY, ENCODING POLYNUCLEOTIDE AND METHODS OF MAKING AND USING THE ANTIBODY FOR IL-4R DETECTION AND DISEASE TREATMENT

(71) Applicant: SHANGHAI NOVAMAB BIOPHARMACEUTICALS CO., LTD., Shanghai (CN)

(72) Inventors: Yakun Wan, Shanghai (CN); Min Zhu, Shanghai (CN); Junwei Gai, Shanghai (CN); Xiaoning Shen, Shanghai (CN)

(73) Assignee: SHANGHAI NOVAMAB BIOPHARMACEUTICALS CO., LTD., Shanghai (CN)

( * ) Notice: Subject to any disclaimer, the term of this patent is extended or adjusted under 35 U.S.C. 154(b) by 83 days.

(21) Appl. No.: 17/772,350

(22) PCT Filed: Jul. 31, 2020

(86) PCT No.: PCT/CN2020/106311
§ 371 (c)(1),
(2) Date: Apr. 27, 2022

(87) PCT Pub. No.: WO2021/082573
PCT Pub. Date: May 6, 2021

(65) Prior Publication Data
US 2022/0411519 A1    Dec. 29, 2022

(30) Foreign Application Priority Data
Oct. 31, 2019    (CN) .......................... 201911054787.9

(51) Int. Cl.
*C07K 16/28*    (2006.01)
*A61K 47/68*    (2017.01)
*C12N 15/85*    (2006.01)

(52) U.S. Cl.
CPC ...... *C07K 16/2866* (2013.01); *A61K 47/6849* (2017.08); *C12N 15/85* (2013.01); *C07K 2317/24* (2013.01); *C07K 2317/35* (2013.01); *C07K 2317/569* (2013.01); *C07K 2319/30* (2013.01); *C12N 2800/107* (2013.01)

(58) Field of Classification Search
CPC ............ C07K 16/2866; C07K 2317/24; C07K 2317/35; C07K 2317/569; C07K 2319/30; A61K 47/6849; C12N 15/85; C12N 2800/107
See application file for complete search history.

(56) References Cited

U.S. PATENT DOCUMENTS 6,156,877 A    12/2000    Ritter et al.

FOREIGN PATENT DOCUMENTS

| CN | 104995212 A | 10/2015 |
|---|---|---|
| CN | 105753987 A | 7/2016 |
| CN | 105924531 A | 9/2016 |
| CN | 106267190 A | 1/2017 |
| CN | 108373505 A | 8/2018 |
| CN | 108409860 A | 8/2018 |
| CN | 110105451 A | 8/2019 |
| WO | 0192340 A2 | 12/2001 |

*Primary Examiner* — Robert S Landsman
(74) *Attorney, Agent, or Firm* — NKL Law; Allen Xue

(57) ABSTRACT

Disclosed is an anti-IL-4R single-domain antibody and the use thereof. In particular, disclosed are a IL-4R single-domain antibody and a VHH chain thereof, a coding sequence encoding the above-mentioned single-domain antibody or the VHH chain thereof, a corresponding expression vector, host cells capable of expressing the single-domain antibody, and a method for producing the single-domain antibody. The single-domain antibody can specifically recognize human and marmoset IL-4R, but does not recognize mouse IL-4R, and the specificity is good; the single-domain antibody can effectively inhibit the proliferation of TF-1 cells and the activation of a pSTAT6 signaling pathway in cells.

21 Claims, 11 Drawing Sheets
Specification includes a Sequence Listing.

SEQUENCE LISTING

<160> NUMBER OF SEQ ID NOS: 20

<210> SEQ ID NO 1
<211> LENGTH: 10
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain CDR1

<400> SEQUENCE: 1

Gly Ser Thr Ser Tyr Arg Tyr Cys Met Ala
1               5                   10

<210> SEQ ID NO 2
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain CDR2

<400> SEQUENCE: 2

Ile Arg Pro Arg Ser Gly Arg Ala
1               5

<210> SEQ ID NO 3
<211> LENGTH: 12
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain CDR3

<400> SEQUENCE: 3

Ala Ala Ser Asp Asn Asp Gly Asn Cys Gln Asp Tyr
1               5                   10

<210> SEQ ID NO 4
<211> LENGTH: 25
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR1

<400> SEQUENCE: 4

Gln Val Gln Leu Gln Glu Ser Gly Gly Gly Ser Val Gln Ala Gly Gly
1               5                   10                  15

Ser Leu Arg Val Ser Cys Ala Ala Ser
            20                  25

<210> SEQ ID NO 5
<211> LENGTH: 15
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR2

<400> SEQUENCE: 5

Trp Phe Arg Gln Ala Pro Gly Lys Glu Arg Glu Ala Val Ala Ser
1               5                   10                  15

<210> SEQ ID NO 6
<211> LENGTH: 38
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR3

<400> SEQUENCE: 6

Tyr Tyr Ala Asp Ser Val Lys Gly Arg Phe Thr Ile Ser Leu Asp Asn
1               5                   10                  15

Ala Lys Asn Thr Leu Tyr Leu Gln Met Asn Ser Leu Lys Pro Glu Asp
            20                  25                  30

Thr Ala Met Tyr Tyr Cys
        35

<210> SEQ ID NO 7
<211> LENGTH: 11
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR4

<400> SEQUENCE: 7

Trp Gly Lys Gly Thr Gln Val Thr Val Ser Ser
1               5                   10

<210> SEQ ID NO 8
<211> LENGTH: 119
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain

<400> SEQUENCE: 8

Gln Val Gln Leu Gln Glu Ser Gly Gly Gly Ser Val Gln Ala Gly Gly
1               5                   10                  15

```
Ser Leu Arg Val Ser Cys Ala Ala Ser Gly Ser Thr Ser Tyr Arg Tyr
            20                  25                  30

Cys Met Ala Trp Phe Arg Gln Ala Pro Gly Lys Glu Arg Glu Ala Val
            35                  40                  45

Ala Ser Ile Arg Pro Arg Ser Gly Arg Ala Tyr Tyr Ala Asp Ser Val
        50                  55                  60

Lys Gly Arg Phe Thr Ile Ser Leu Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Ser Asp Asn Asp Gly Asn Cys Gln Asp Tyr Trp Gly Lys Gly
            100                 105                 110

Thr Gln Val Thr Val Ser Ser
        115
```

<210> SEQ ID NO 9
<211> LENGTH: 357
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: polynucleotide

<400> SEQUENCE: 9

```
caggtgcagc tgcaggagtc tgggggaggc tcggtgcagg ctggagggtc tctgagagtc      60
tcctgtgcag cctctggatc cacctcctat agatactgta tggcctggtt ccgccaggct     120
ccagggaagg agcgcgaggc ggtcgcatcc attcgcccac gtagtggtag ggcatactat     180
gccgactccg tgaagggccg attcaccatc tccctagaca cgccaagaa cacgctgtat      240
ctgcaaatga acagtctgaa acctgaggac actgccatgt actactgtgc ggcctccgac     300
aacgacggta attgccagga ctactggggc aaaggaaccc aggtcaccgt ctcctca        357
```

<210> SEQ ID NO 10
<211> LENGTH: 25
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR1

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 11
<211> LENGTH: 15
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR2

<400> SEQUENCE: 11

```
Trp Phe Arg Gln Ala Pro Gly Lys Gly Leu Glu Ala Val Ala Ser
1               5                   10                  15

<210> SEQ ID NO 12
<211> LENGTH: 38
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR3

<400> SEQUENCE: 12

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
                20                  25                  30

Thr Ala Val Tyr Tyr Cys
            35

<210> SEQ ID NO 13
<211> LENGTH: 11
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain FR4

<400> SEQUENCE: 13

Trp Gly Lys Gly Thr Leu Val Thr Val Ser Ser
1               5                   10

<210> SEQ ID NO 14
<211> LENGTH: 119
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: VHH chain

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Ser Tyr Arg Tyr
                20                  25                  30

Cys Met Ala Trp Phe Arg Gln Ala Pro Gly Lys Gly Leu Glu Ala Val
            35                  40                  45

Ala Ser Ile Arg Pro Arg Ser Gly Arg Ala Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Asp Asn Asp Gly Asn Cys Gln Asp Tyr Trp Gly Lys Gly
            100                 105                 110

Thr Leu Val Thr Val Ser Ser
        115
```

<210> SEQ ID NO 15
<211> LENGTH: 357
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: nucleotide sequence encoding VHH chain

<400> SEQUENCE: 15

```
caggtgcagc tgcaggagag cggcggcggc ctggtgcagc ccggcggcag cctgaggctg      60
agctgcgccg ccagcggcag caccagctac aggtactgca tggcctggtt caggcaggcc     120
cccggcaagg gcctggaggc cgtggccagc atcaggccca ggagcggcag ggcctactac     180
gccgacagcg tgaagggcag gttcaccatc agcagggaca cagcaagaa caccctgtac     240
ctgcagatga acagcctgag ggccgaggac accgccatgt actactgcgc cgccagcgac     300
aacgacggca actgccagga ctactggggc aagggcaccc tggtgaccgt gagcagc       357
```

<210> SEQ ID NO 16
<211> LENGTH: 346
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: bivalent anti-IL-4R single-domain antibody

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Ser Tyr Arg Tyr
            20                  25                  30

Cys Met Ala Trp Phe Arg Gln Ala Pro Gly Lys Gly Leu Glu Ala Val
        35                  40                  45

Ala Ser Ile Arg Pro Arg Ser Gly Arg Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Asp Asn Asp Gly Asn Cys Gln Asp Tyr Trp Gly Lys Gly
            100                 105                 110

Thr Leu Val Thr Val Ser Ser Glu Ser Lys Tyr Gly Pro Pro Cys Pro
        115                 120                 125

Pro Cys Pro Ala Pro Glu Phe Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220
```

```
Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Glu
            245                 250                 255

Glu Met Thr Lys Asn Gln Val Ser Leu Thr Cys Leu Val Lys Gly Phe
        260                 265                 270

Tyr Pro Ser Asp Ile Ala Val Glu Trp Glu Ser Asn Gly Gln Pro Glu
    275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly
            340                 345
```

```
<210> SEQ ID NO 17
<211> LENGTH: 1038
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: nucleotide sequence encoding huNb103

<400> SEQUENCE: 17
gaggtgcagc tggtggagtc cggcggcggc ctggtgcagc cggcggctc cctgaggctg      60 tcctgcgccg cctccggctc cacctcctac aggtactgca tggcctggtt caggcaggcc     120
cccggcaagg gcctggaggc cgtggcctcc atcaggccca ggtccggcag ggcctactac     180
gccgactccg tgaagggcag gttcaccatc tccaggaca actccaagaa cacccctgtac     240 ctgcagatga actccctgag gccgaggac accgccgtgt actactgcgc cgcctccgac     300
aacgacggca ctgccagga ctactgggcc aagggcaccc tggtgaccgt gtcctccgag      360
tccaagtacg ccccccctg ccccccctgc ccgccccccg agttcctggg cggccctcc      420 gtgttcctgt tccccccaa gcccaaggac accctgatga tctccaggac ccccgaggtg     480
acctgcgtgg tggtggacgt gtcccaggag accccgaggg tgcagttcaa ctggtacgtg    540
gacggcgtgg aggtgcacaa cgccaagacc aagcccaggg aggagcagtt caactccacc    600
tacagggtgg tgtccgtgct gaccgtgctg caccaggact ggctgaacgg caaggagtac    660
aagtgcaagg tgtccaacaa gggcctgccc tcctccatcg agaagaccat ctccaaggcc    720
aagggccagc ccaggagcc ccaggtgtac accctgcccc cctccgagga gatgaccaag    780
aaccaggtgt ccctgacctg cctggtgaag ggcttctacc cctccgacat cgccgtggag    840
tgggagtcca acggccagcc cgagaacaac tacaagacca ccccccccgt gctggactcc    900
gacggctcct tcttcctgta ctccaggctg accgtggaca agtccaggtg gcaggagggc    960
aacgtgttct cctgctccgt gatgcacgag gccctgcaca accactacac ccagaagtcc   1020
ctgtccctgt ccctgggc                                                 1038

<210> SEQ ID NO 18
<211> LENGTH: 9
<212> TYPE: PRT
<213> ORGANISM: Artificial sequence
<220> FEATURE:
```

```
<223> OTHER INFORMATION: synthesized
<220> FEATURE:
<221> NAME/KEY: misc_feature
<223> OTHER INFORMATION: linker

<400> SEQUENCE: 18

Gly Gly Gly Gly Ser Gly Gly Gly Ser
1               5

<210> SEQ ID NO 19
<211> LENGTH: 474
<212> TYPE: PRT
<213> ORGANISM: Artificial sequence
<220> FEATURE:
<223> OTHER INFORMATION: synthesized
<220> FEATURE:
<221> NAME/KEY: misc_feature
<223> OTHER INFORMATION: tetravalent single-domain antibody

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Ser Tyr Arg Tyr
            20                  25                  30

Cys Met Ala Trp Phe Arg Gln Ala Pro Gly Lys Gly Leu Glu Ala Val
        35                  40                  45

Ala Ser Ile Arg Pro Arg Ser Gly Arg Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ser Asp Asn Asp Gly Asn Cys Gln Asp Tyr Trp Gly Lys Gly
            100                 105                 110

Thr Leu Val Thr Val Ser Ser Gly Gly Gly Ser Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Ser Thr Ser Tyr Arg Tyr
145                 150                 155                 160

Cys Met Ala Trp Phe Arg Gln Ala Pro Gly Lys Gly Leu Glu Ala Val
                165                 170                 175

Ala Ser Ile Arg Pro Arg Ser Gly Arg Ala Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Ala Ser Asp Asn Asp Gly Asn Cys Gln Asp Tyr Trp Gly Lys Gly
225                 230                 235                 240

Thr Leu Val Thr Val Ser Ser Glu Ser Lys Tyr Gly Pro Pro Cys Pro
                245                 250                 255

Pro Cys Pro Ala Pro Glu Phe Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser Gln Glu Asp Pro Glu Val Gln Phe
    290                 295                 300
```

Asn Trp Tyr Val Asp Gly Val Glu Val His Asn Ala Lys Thr Lys Pro
305                 310                 315                 320

Arg Glu Glu Gln Phe Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Gly Leu Pro Ser Ser Ile Glu Lys Thr Ile Ser Lys Ala
        355                 360                 365

Lys Gly Gln Pro Arg Glu Pro Gln Val Tyr Thr Leu Pro Pro Ser Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Arg Leu Thr Val Asp Lys Ser Arg Trp Gln Glu Gly
        435                 440                 445

Asn Val Phe Ser Cys Ser Val Met His Glu Ala Leu His Asn His Tyr
    450                 455                 460

Thr Gln Lys Ser Leu Ser Leu Ser Leu Gly
465                 470

<210> SEQ ID NO 20
<211> LENGTH: 1422
<212> TYPE: DNA
<213> ORGANISM: Artificial sequence
<220> FEATURE:
<223> OTHER INFORMATION: synthesized
<220> FEATURE:
<221> NAME/KEY: misc_feature
<223> OTHER INFORMATION: nucleotide sequence encoding tetravalent
      single-domain antibody

<400> SEQUENCE: 20
gaagtgcagc tggtggagtc tgaggcggc ctggtgcagc ctggaggctc tctgagactg     60
tcttgtgctg cctctggcag cacatcttac agatactgca tggcctggtt cagacaggct    120
cctggcaagg gcctggaggc cgtggcctct atcagaccta gatctggaag ggcctactat    180
gctgacagcg tgaagggcag gttcacaatc tctagagata actctaagaa cactctgtac    240
ctgcagatga actctctgag agcagaggat accgccgtgt actactgtgc cgccagcgat    300
aacgatggaa actgtcagga ttattggggc aagggaacac tggtgacagt gtctagcggc    360
ggaggcggaa gcggcggcgg aagcgaggtg cagctggtgg agtccggagg cggcctggtg    420
cagccaggag gcagcctgag actgagctgc gccgccagcg gcagcacatc ttacaggtac    480
tgcatggcct ggtttaggca ggctccagga aagggcctgg aggccgtggc cagcattaga    540
cccaggagcg gcagagctta ctacgccgac tctgtgaagg gcagattcac catcagcaga    600
gataacagta agaacaccct gtacctgcag atgaatagcc tgagagctga ggataccgct    660
gtgtattact gtgctgcctc tgacaacgac ggcaactgtc aggattactg ggaaagggc    720 acactggtga cagtgtcttc tgagtctaag tacggcccac cttgtcctcc ttgccctgcc    780
cccgagtttc tgggaggccc atctgtgttt ctgttccctc ctaagcctaa ggacacactg    840
atgatttcta gaacacctga ggtgacttgt gtggtggtgg acgtgagcca ggaggaccct    900
gaggtgcagt ttaactggta cgtggacggc gtggaggtgc acaacgccaa gaccaagcct    960

```
agagaggagc agttcaacag cacctacaga gtggtgagcg tgctgaccgt gctgcaccag    1020
gactggctga acggcaagga gtacaagtgc aaggtgagca acaagggact gccatctagc    1080
atcgagaaga ccatctctaa ggccaagggc cagccaagag agccacaggt gtacaccctg    1140
cctccttctg aggagatgac caagaaccag gtgtctctga cctgtctggt gaagggcttc    1200
taccctagcg acatcgccgt ggagtgggag tccaacggcc agcctgagaa caactacaag    1260
acaaccccac ctgtgctgga tagcgacggc agcttctttc tgtacagcag actgaccgtg    1320
gataagtcta ggtggcagga gggaaacgtg tttagctgtt ctgtgatgca cgaggccctg    1380
cacaaccact acacacagaa gagcctgtct ctgagcctgg gc                       1422
```

ANTI-INTERLEUKIN-4 RECEPTOR (IL-4R) SINGLE-DOMAIN ANTIBODY, ENCODING POLYNUCLEOTIDE AND METHODS OF MAKING AND USING THE ANTIBODY FOR IL-4R DETECTION AND DISEASE TREATMENT

INCORPORATION OF SEQUENCE LISTING

This application contains a sequence listing in Computer Readable Form (CRF). The CFR file contains the sequence listing entitled "PBA4085425-SequenceListing.txt", which was created on Apr. 27, 2022, and is 18,704 bytes in size. The information in the sequence listing is incorporated herein by reference in its entirety.

TECHNICAL FIELD

The present invention relates to the technical field of biomedicine or bio-pharmaceuticals, and more particularly relates to an anti-IL-4R single-domain antibody and use thereof.

BACKGROUND

Interleukin-4 (IL-4, also known as B cells stimulating factor or BSF-1) is a cytokine mainly produced by activated T cells, monocytes, basophils, mast cells, and eosinophils. All biological functions of IL-4 are mediated by IL-4R on the surface of effector cells. IL-4R consists of α and γ subunits, and the interleukin-4 receptor a subunit (IL-4Ra) is located in the chromosome 16P12 1.1-PI1.2 region, which is also an asthma susceptibility region. Gene polymorphisms in this region are associated with hypersensitivity and elevated serum IgE levels. In addition, IL-4Ra is a common component of the IL-4 and IL-13 gene receptor complex. Studies have shown that IL-4Ra gene polymorphisms are associated with asthma, elevated serum IgE levels, and atopic dermatitis.

Asthma is a common respiratory disease and also a frequently-occurring disease. Asthma is a chronic inflammatory disease of the airway involving a variety of cells (e.g., eosinophils, mast cells, T lymphocytes, neutrophil airway epithelial cells, etc.) and cellular components. It has many different molecular pathological and physiological phenotypes. Asthma is a heterogeneous disease, which can be divided into allergic asthma and non-allergic asthma. In allergic asthma, abnormally high expression of type II helper T cytokine (Th2) has been found in bronchus, and it has been proved that Th2 cytokine fully mediates the occurrence and development of inflammatory response and promotes pathological changes of respiratory tract, etc., which is an ideal target for anti-asthma. Th2 subsets mainly produce IL-4, IL-5, IL-6, IL-10, IL-13, etc. IL-4R plays an important biological role in asthma mainly through the combination of IL-4 and IL-13, etc.

Atopic dermatitis (AD) is the most common inflammatory skin disease, with an incidence of 15%-30% in children and 2%-10% in adults. It has the characteristics of early onset, long duration and severe pruritus, which will have a serious impact on the quality of life of patients. Th2 cytokines are significantly elevated in patients with skin lesions to promote the secretion of IL-4 and IL-13, and mediate the downstream signal transduction by co-receptor IL-4Ra.

Currently, antibody drugs targeting hIL-4R have entered clinical trials. For example, Dupilumab is an anti-IL-4Rα monoclonal antibody, which can block the binding of IL-4 and IL-13 to IL-4Rα, thus blocking the downstream signaling pathway to inhibit the development of chronic inflammation in dermatitis. It has shown good efficacy in the treatment of atopic dermatitis in phase II clinical trials. Besides the Dupilumab, the drug CBP201 under the development of Suzhou Connect Biopharm Co., LTD., published in patent CN201610399254.4, is also a monoclonal antibody against IL-4Rα. It has been filed in Australia for phase I clinical trials.

So far, there is no single-domain antibody drug targeting hIL-4R has been announced on the market. Single-domain antibody (nanobody, Nb), that is heavy chain single-domain antibody VHH (variable domain of heavy-chain antibody), is a heavy-chain antibody (HCAb) that naturally lacks the light chain in camels. The single-domain antibody consisting of only one heavy chain variable region obtained by cloning its variable regions is the smallest unit of stable binding antigen with complete function at present. Single-domain antibodies have the advantages of high stability, good aqueous solubility, simple humanization, high targeting and strong penetration, and play a huge role in immune experiment, diagnosis and treatment. Single-domain antibodies are gradually becoming a new rising force in the diagnosis and treatment of new generation of antibodies.

It has become an urgent problem to be solved to develop a new anti-IL-4R single-domain antibody with better specificity, blocking efficacy, better clinical efficacy and simple production, so as to reduce the production cost and lighten the medication burden of patients.

SUMMARY OF INVENTION

The purpose of the present invention is to provide an anti-IL-4R single-domain antibody and use thereof.

Specifically, the purpose of the present invention is to provide a single-domain antibody that can specifically bind to IL-4R protein.

In the first aspect of the present invention, it provides a complementarity determining region or CDR of an anti-IL-4R single-domain antibody VHH chain, wherein the complementarity determining region CDR of the VHH chain comprise CDR1 as shown in SEQ ID NO: 1, CDR2 as shown in SEQ ID NO: 2, and CDR3 as shown in SEQ ID NO: 3.

In another preferred embodiment, the CDR1, CDR2 and CDR3 are separated by the framework regions FR1, FR2, FR3 and FR4.

In the second aspect of the present invention, it provides a VHH chain of an anti-IL-4R single-domain antibody, wherein the VHH chain comprises the framework regions FRs and the complementarity determining regions CDRs according to the first aspect of the present invention.

In another preferred embodiment, wherein the framework regions FRs comprise:
(a) FR1 as shown in SEQ ID NO: 4, FR2 as shown in SEQ ID NO: 5, FR3 as shown in SEQ ID NO: 6, and FR4 as shown in SEQ ID NO: 7; or
(b) FR1 as shown in SEQ ID NO: 10, FR2 as shown in SEQ ID NO: 11, FR3 as shown in SEQ ID NO: 12, and FR4 as shown in SEQ ID NO: 13.

In another preferred embodiment, the VHH chain of the anti-IL-4R single-domain antibody is as shown in SEQ ID NO: 8 or 14.

In addition, it further provides a novel heavy chain variable region of the anti-IL-4R single-domain antibody, wherein the heavy chain variable region comprises CDR1 as shown in SEQ ID NO: 1, CDR2 as shown in SEQ ID NO: 2, and CDR3 as shown in SEQ ID NO: 3.

In the third aspect of the present invention, it provides an anti-IL-4R single-domain antibody, which against the interleukin 4 receptor (IL-4R) epitope, and has a VHH chain according to the second aspect of the present invention.

In another preferred embodiment, the anti-IL-4R single-domain antibody includes monomer, bivalent antibody, tetravalent antibody, and/or multivalent antibody.

In another preferred embodiment, the anti-IL-4R single-domain antibody comprises one or more VHH chains of amino acid sequences as shown in SEQ ID NO: 8 or SEQ ID NO: 14.

In another preferred embodiment, the VHH chain sequence of the anti-IL-4R single-domain antibody is shown as SEQ ID NO: 8 and/or SEQ ID NO: 14.

In another preferred embodiment, the anti-IL-4R single-domain antibody comprises two VHH chains of amino acid sequences as shown in SEQ ID NO: 8 or SEQ ID NO: 14.

In another preferred embodiment, the anti-IL-4R single-domain antibody comprises four VHH chains of amino acid sequences as shown in SEQ ID NO: 8 or SEQ ID NO: 14.

In another preferred embodiment, the anti-IL-4R single-domain antibody has VHH chains of amino acid sequences as shown in SEQ ID NO: 8 and/or SEQ ID NO: 14.

In another preferred embodiment, the two VHH chains of amino acid sequences as shown in SEQ ID NO: 14 are linked via a linker.

In another preferred embodiment, the four VHH chains of amino acid sequences as shown in SEQ ID NO: 14 are linked via a linker.

In another preferred embodiment, the linker is selected from the following sequences: $(G_aS_b)_x$-$(G_mS_n)_y$, wherein each of a, b, m, n, x, y is 0 or 1 or 1 or 2 or 3 or 4 or 5 or 6 or 7 or 8 or 9 or 10 (more preferably, a=4, while b=1, m=3, and n=1).

In another preferred embodiment, the linker is selected from the group consisting of GGGGSGGGS (SEQ ID NO: 18).

In another preferred embodiment, the amino acid sequence of the anti-IL-4R single-domain antibody is shown as SEQ ID NO: 19.

In the fourth aspect of the present invention, it provides an anti-IL-4R single-domain antibody Fc fusion protein, wherein the structure from N-terminus to C-terminus of the fusion protein is shown in Formula Ia or Ib:

A-L-B    (Ia);

B-L-A    (Ib);

wherein,

A is the anti-IL-4R single-domain antibody of the third aspect of the present invention;

B is the Fc fragment of IgG; and

L is none or a flexible linker.

In another preferred embodiment, the flexible linker is a peptide linker.

In another preferred embodiment, the peptide linker has 1-50 amino acids, more preferably 1-20 amino acids.

In another preferred embodiment, the Fc fragment of IgG includes the Fc fragment of human IgG.

In another preferred embodiment, the peptide linker has the structure of (GGGGS)n, wherein n is a positive integer from 1 to 5.

In another preferred embodiment, the Fc fragment of IgG includes the Fc fragment of human IgG.

In another preferred embodiment, the Fc fragment of IgG is selected from the group consisting of Fc fragment of IgG1, IgG2, IgG3, IgG4, and a combination thereof.

In another preferred embodiment, the Fc fragment of IgG is IgG4.

In another preferred embodiment, the amino acid sequence of the Fc fragment is shown at positions 120-346 in SEQ ID NO: 16.

In another preferred embodiment, the amino acid sequence of the fusion protein is shown as SEQ ID NO: 16 or SEQ ID NO: 19.

In another preferred embodiment, the fusion protein is a single-domain antibody Fc fusion protein against an IL-4R epitope.

In the fifth aspect of the present invention, it provides a polynucleotide encoding a protein selected from the group consisting of: the CDR region of the anti-IL-4R single-domain antibody VHH chain according to the first aspect of the present invention, the VHH chain of the anti-IL-4R single-domain antibody according to the second aspect of the present invention, or the anti-IL-4R single-domain antibody according to the third aspect of the present invention, or the anti-IL-4R single-domain antibody Fc fusion protein according to the fourth aspect of the present invention.

In another preferred embodiment, the polynucleotide has a nucleotide sequence as shown in SEQ ID NO: 9, or 15.

In another preferred embodiment, the polynucleotide has a nucleotide sequence as shown in SEQ ID NO: 20.

In another preferred embodiment, the polynucleotide comprises DNA or RNA.

In the sixth aspect of the present invention, it provides an expression vector containing the polynucleotide according to the fifth aspect of the present invention.

In another preferred embodiment, the expression vector is selected from the group consisting of DNA, RNA, viral vector, plasmid, transposon, other gene transfer system, and a combination thereof.

Preferably, the expression vector comprises viral vector, such as lentivirus, adenovirus, AAV virus, retrovirus, and a combination thereof.

In the seventh aspect of the present invention, it provides a host cell containing the expression vector according to the sixth aspect of the present invention, or in which the polynucleotide according to the fifth aspect of the present invention is integrated into a genome thereof.

In another preferred embodiment, the host cell comprises a prokaryotic cell or an eukaryotic cell.

In another preferred embodiment, the host cell is selected from the group consisting of: *Escherichia coli*, a yeast cell, a mammalian cell, bacteriophage, and a combination thereof.

In another preferred embodiment, the prokaryotic cell is selected from the group consisting of: *Escherichia coli, Bacillus subtilis, Lactobacillus, Streptomyces, Proteus mirabilis*, and a combination thereof.

In another preferred embodiment, the eukaryotic cell is selected from the group consisting of: *Pichia pastoris, Saccharomyces cerevisiae, Schizosaccharomyces pombe, Trichoderma*, and a combination thereof.

In another preferred embodiment, the eukaryotic cell is selected from the group consisting of: an insect cell such as a grass armyworm cell, a plant cell such as a tobacco cell, a BHK cell, a CHO cell, a COS cell, a myeloma cell, and a combination thereof.

In another preferred embodiment, the host cell is preferably a mammalian cell, and more preferably a HEK293 cell, a CHO cell, a BHK cell, a NSO cell, or a COS cell.

In another preferred embodiment, the host cell is *Pichia pastoris*.

In the eighth aspect of the present invention, it provides a method for producing an anti-IL-4R single-domain antibody or Fc fusion protein thereof, comprising the steps of:
(a) cultivating the host cell according to the seventh aspect of the present invention under conditions suitable for production of a single-domain antibody or the Fc fusion protein thereof, thereby obtaining a culture containing the anti-IL-4R single-domain antibody or the Fc fusion protein thereof; and
(b) isolating or recovering the anti-IL-4R single-domain antibody or the Fc fusion protein thereof from the culture; and
(c) optionally, purifying and/or modifying the IL-4R single-domain antibody or the Fc fusion protein thereof in the step (b).

In another preferred embodiment, the anti-IL-4R single-domain antibody has an amino acid sequence as shown in SEQ ID NO: 8 or 14.

In another preferred embodiment, the anti-IL-4R single-domain antibody has an amino acid sequence as shown in SEQ ID NO: 19.

In the ninth aspect of the present invention, it provides an immunoconjugate containing:
(a) the VHH chain of the anti-IL-4R single-domain antibody according to the second aspect of the present invention, or the anti-IL-4R single-domain antibody according to the third aspect of the present invention; or the anti-IL-4R single-domain antibody Fc fusion protein according to the fourth aspect of the present invention; and
(b) a coupling moiety selected from the group consisting of: a detectable label, drug, toxin, cytokine, radionuclide, enzyme, gold nanoparticle/nanorod, magnetic nanoparticle, viral capsid protein or VLP, and a combination thereof.

In another preferred embodiment, the radionuclide comprises:
(i) a diagnostic isotope which is selected from the group consisting of Tc-99m, Ga-68, F-18, I-123, I-125, I-131, In-111, Ga-67, Cu-64, Zr-89, C-11, Lu-177, Re-188, and a combination thereof; and/or
(ii) a therapeutic isotope which is selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133, Yb-169, Yb-177, and a combination thereof.

In another preferred embodiment, the coupling moiety is a drug or toxin.

In another preferred embodiment, the drug is a cytotoxic drug.

In another preferred embodiment, the cytotoxic drug is selected from the group consisting of an antitubulin drug, DNA sulcus binding reagent, DNA replication inhibitor, alkylation reagent, antibiotic, folic acid antagonist, antimetabolite, chemotherapeutic sensitizer, topoisomerase inhibitor, *vinca* alkaloids, and a combination thereof.

In another preferred embodiment, the particularly useful cytotoxic drug includes, for example, DNA sulcus binding reagent, DNA alkylation reagent, and tubulin inhibitor. The typical cytotoxic drug includes, such as auristatins, camptothecins, duocarmycins, etoposides, maytansines and maytansinoids (such as DM1 and DM4), taxanes, benzodiazepines or benzodiazepine containing drugs (such as PBDs, indolinobenzodiazepines and oxazolidinobenzodiazepines), *vinca* alkaloids, and a combination thereof.

In another preferred embodiment, the toxin is selected from the group consisting of otostatins (e.g., otostatin E, otostatin F, MMAE and MMAF), aureomycin, metametanol, ricin toxin, ricin A-chain, cobustatin, docamicin, dorastatin, doxorubicin, daunorubicin, paclitaxel, cisplatin, cc1065, ethidium bromide, mitomycin, etoposide, tenoposide, vincristine, vinblastine, colchicine, dihydroxy anthrax dione, actinomycin, diphtheria toxin, *pseudomonas* ectotoxin (PE)A, PE40, Acacia bean toxin, Acacia bean toxin A chain, capsule root toxin A chain, α-tocsin, Atractylodes toxin, mitogellin, retstrictocin, phenomycin, enomycin, curicin, battocin, Kazinomycin, *Sapaonaria Officinalis* inhibitor, glucocorticoids, and a combination thereof.

In another preferred embodiment, the coupling moiety is a detectable label.

In another preferred embodiment, the coupling moiety is selected the group consisting of a fluorescent or luminescent label, radioactive label, MRI (magnetic resonance imaging) or CT (electronic computer X-ray tomography) contrast agent, or enzyme capable of producing a detectable product, radionuclide, biotoxin, cytokine (such as IL-2, etc.), antibody, antibody Fc fragment, antibody scFv fragment, gold nanoparticle/nanorod, virus particle, liposome, nanomagnetic particle, prodrug activating enzyme (e.g., DT-diaphorase (DTD) or biphenyl hydrolase-like protein (BPHL)), or nanoparticle in any form.

In another preferred embodiment, the immunoconjugate contains: a multivalent (e.g., bivalent or tetravalent) VHH chain of the anti-IL-4R single domain antibody according to the second aspect of the present invention, or the anti-IL-4R single-domain antibody according to the third aspect of the present invention, or the anti-IL-4R single-domain antibody Fc fusion protein according to the fourth aspect of the present invention.

In another preferred embodiment, the multivalent means that the amino acid sequence of the immunoconjugate contains multiple repeats of the VHH chain of the anti-IL-4R single-domain antibody according to the second aspect of the present invention, or the anti-IL-4R single-domain antibody according to the third aspect of the present invention, or the anti-IL-4R single-domain antibody Fc fusion protein according to the fourth aspect of the present invention.

In the tenth aspect of the present invention, it provides a use of the VHH chain of the anti-IL-4R single-domain antibody according to the second aspect of the present invention or the anti-IL-4R single-domain antibody according to the third aspect of the present invention, or the anti-IL-4R single-domain antibody Fc fusion protein according to the fourth aspect of the present invention for preparing a medicine used to prevent or treat diseases or disorders associated with IL-4/IL-4R signaling transduction.

In the eleventh aspect of the present invention, it provides a pharmaceutical composition comprising:
(i) the complementarity determining region CDR of the anti-IL-4R single-domain antibody VHH chain according to the first aspect of the present invention, the VHH chain of the anti-IL-4R single-domain antibody according to the second aspect of the present invention, the anti-IL-4R single-domain antibody according to the third aspect of the present invention, or the anti-IL-4R single-domain antibody Fc fusion protein according to the fourth aspect of the present invention, or the immunoconjugate according to the ninth aspect of the present invention; and
(ii) a pharmaceutically acceptable carrier.

In another preferred embodiment, the coupling moiety of the immunoconjugate is a drug, toxin, and/or therapeutic isotope.

In another preferred embodiment, the pharmaceutical composition further comprises another drug for the treatment of asthma, atopic dermatitis, arthritis, allergic rhinitis and/or eczema, such as corticosteroid (TCS), nedolomide sodium, sodium glycyrrhizin, theophylline, leukotriene receptor antagonist, and a combination thereof.

In another preferred embodiment, the pharmaceutical composition is an injection formulation.

In another preferred embodiment, the pharmaceutical composition is used for preparing a medicine for preventing and/or treating a disease or disorder associated with IL-4/IL-4R signaling transduction.

In another preferred embodiment, the disease or disorder includes but is not limited to asthma, atopic dermatitis, arthritis, allergic rhinitis, eczema, etc.

In the twelfth aspect of the present invention, it provides one or more uses of the anti-IL-4R single-domain antibody according to the third aspect of the present invention, and/or the anti-IL-4R single-domain antibody Fc fusion protein according to the fourth aspect of the present invention for preparing (a) a medicine for preventing and/or treating a disease or disorder associated with IL-4/IL-4R signaling transduction;
(b) for detection of human IL-4R molecules;
(c) for flow cytometry detection;
(d) for cellular immunofluorescence detection.

In another preferred embodiment, the use is diagnostic and/or non-diagnostic, and/or therapeutic and/or non-therapeutic.

In the thirteenth aspect of the present invention, it provides an antibody including one or more VHH chains of the anti-IL-4R single-domain antibody according to the second aspect of the present invention.

In another preferred embodiment, the antibody includes two VHH chains of the anti-IL-4R single-domain antibody according to the second aspect of the present invention.

In another preferred embodiment, the antibody includes VHH chains of the anti-IL-4R single-domain antibody according to the second aspect of the present invention.

In another preferred embodiment, the antibody includes heavy chain variable region VHH according to the second aspect of the present invention.

In another preferred embodiment, the antibody can specifically target IL-4R proteins with the correct spatial structure.

In another preferred embodiment, the antibody can recognize human and marmoset IL-4R, but not mouse IL-4R.

In another preferred embodiment, the antibody can effectively inhibit the proliferation inhibition, and the inhibitory activity is significantly superior to that of the commercial single-domain antibody Dupilumab.

In another preferred embodiment, the antibody can effectively inhibit the activation of the pSTAT6 signal pathway in cell, and the inhibitory activity is significantly higher than that of the commercial single-domain antibody Dupilumab.

In another preferred embodiment, the antibody is a single-domain antibody.

In the fourteenth aspect of the present invention, it provides a recombinant protein, which comprises:

(i) the VHH chain according to the second aspect of the present invention, or the anti-IL-4R single-domain antibody according to the third aspect of the present invention; or the anti-IL-4R single-domain antibody Fc fusion protein according to the fourth aspect of the present invention, and (ii) an optional tag sequence to aid expression and/or purification.

In another preferred embodiment, the tag sequence comprises Fc tag, HA tag, and 6His tag.

In another preferred embodiment, the recombinant protein specifically binds to IL-4R protein.

In the fifteenth aspect of the present invention, it provides a use of the VHH chain of the anti-IL-4R single-domain antibody according to the second aspect of the present invention, the anti-IL-4R single-domain antibody according to the third aspect of the present invention, or the anti-IL-4R single-domain antibody Fc fusion protein according to the fourth aspect of the present invention, or the immunoconjugate according to the ninth aspect of the present invention for preparation of a medicament, reagent, detection plate or kit;

wherein the reagent, detection plate or kit is used for detecting IL-4R protein in the sample;

wherein the medicament is used for treating or preventing a disease or disorder associated with IL-4/IL-4R signaling transduction.

In another preferred embodiment, the disease or disorder includes but is not limited to asthma, atopic dermatitis, arthritis, allergic rhinitis, eczema, etc.

In another preferred embodiment, the detection includes flow cytometry detection and cellular immunofluorescence detection.

In the sixteenth aspect of the present invention, it provides a method for treating a disease, comprising administrating to a subject in need the single-domain antibody according to the third aspect of the present invention, or the anti-IL-4R single-domain antibody Fc fusion protein according to the fourth aspect of the present invention, or the immunoconjugate according to the ninth aspect of the present invention.

In another preferred embodiment, the subject includes a mammal, such as human, marmoset.

In the seventeenth aspect of the present invention, it provides a method for detecting IL-4R protein in a sample, which comprises the steps of:

(1) contacting the sample with the VHH chain according to the second aspect of the present invention, the single-domain antibody according to the third aspect of the present invention, the anti-IL-4R single-domain antibody Fc fusion protein according to the fourth aspect of the present invention, or the immunoconjugate according to the ninth aspect of the present invention;

(2) detecting whether an antigen-antibody complex is formed, wherein the formation of the complex indicates the presence of IL-4R protein in the sample.

In another preferred embodiment, the method is a non-diagnostic and non-therapeutic method.

In the eighteenth aspect of the present invention, it provides an IL-4R protein detection reagent, which comprises:

(i) the VHH chain according to the second aspect of the present invention, the single-domain antibody according to the third aspect of the present invention, or the anti-IL-4R single-domain antibody Fc fusion protein according to the fourth aspect of the present invention, or the immunoconjugate according to the ninth aspect of the present invention; and (ii) a detectologically acceptable carrier.

In another preferred embodiment, the coupling moiety of the immunoconjugate is a diagnostic isotope.

In another preferred embodiment, the detectologically acceptable carrier is nontoxic, inert aqueous carrier medium.

In another preferred embodiment, the detection reagent includes one or more reagents selected from the group consisting of isotope tracer, contrast agent, flow detection reagent, cell immunofluorescence detection reagent, nano-magnetic particle and imaging agent.

In another preferred embodiment, the detection reagent is used to detect in vivo.

In another preferred embodiment, the form of the detection reagent is liquid or powder (such as aqueous solution, injection, lyophilized powder, tablet, containing agent, inhalant).

In the nineteenth aspect of the present invention, it provides a kit to detect the IL-4R protein, which comprises the immunoconjugate according to the ninth aspect of the present invention, or the detection reagent according to the eighteenth aspect of the present invention, and a specification.

In another preferred embodiment, the specification indicates that the kit is used to non-invasively detect IL-4R expression in the subject to be tested.

In the twentieth aspect of the present invention, it provides a use of immunoconjugate according to the ninth aspect of the present invention for preparing the contrast agent to detect the IL-4R protein in vivo.

In another preferred embodiment, the detection is used for the diagnosis or prognosis of asthma, atopic dermatitis, arthritis, allergic rhinitis, eczema, etc.

In the twenty-first aspect of the present invention, it provides a framework regions FRs of the VHH chain of the anti-IL-4R single-domain antibody, wherein the framework region FRs of the VHH chain consist of FR1 as shown in SEQ ID NO:4, FR2 as shown in SEQ ID NO: 5, FR3 as shown in SEQ ID NO: 6, and FR4 as shown in SEQ ID NO: 7; or FR1 as shown in SEQ ID NO: 10, FR2 as shown in SEQ ID NO: 11, FR3 as shown in SEQ ID NO: 12, and FR4 as shown in SEQ ID NO: 13.

In the twenty-two aspect of the present invention, it provides a method for treatment of a disease or disorder associated with IL-4/IL-4R signaling transduction by administrating the pharmaceutical composition of the eleventh aspect of the present invention to a subject in need.

In another preferred embodiment, the subject includes a mammal, such as human.

It should be understood that, within the scope of the present invention, the technical features specifically described above and below (such as the Examples) can be combined with each other, thereby constituting a new or preferred technical solution which needs not be redundantly described one by one.

DETAILED DESCRIPTION OF INVENTION

Figure 1:
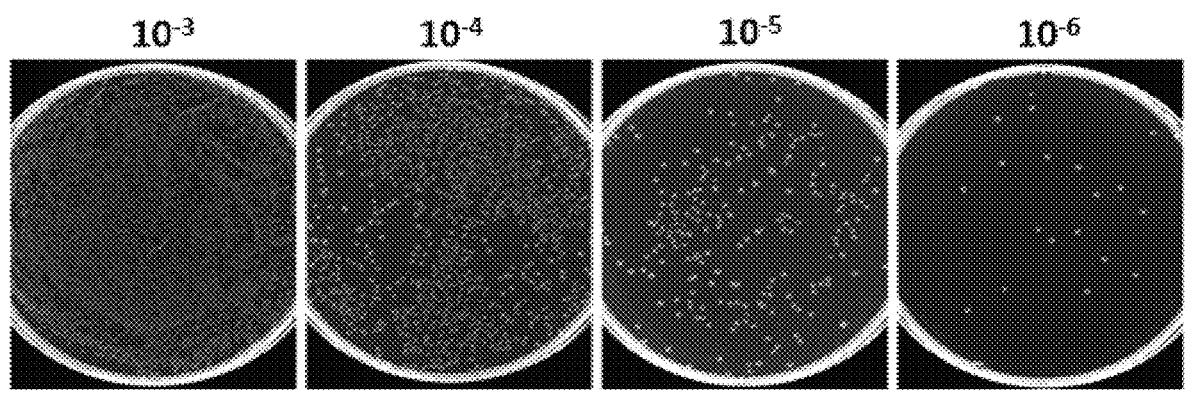
FIG. 1 shows the capacity of the phage display IL-4R single-domain antibody library. The clone number of the constructed library was grown by gradient dilution coating plate, and the calculated library capacity is $1.1 \times 10^9$ CFU.

After extensive and intensive researches and lots of screening, the present inventors have successfully obtained a class of anti-IL-4R single-domain antibodies. The experimental results show that the single-domain antibody of the present invention can specifically recognize IL-4R, and has good specificity. It can effectively recognize human and marmoset IL-4R, but not mouse IL-4R. It also can effectively inhibit the proliferation of the TF-1 cells and the activation of the pSTAT6 signal pathway in cells. The singe-domain antibody of the present invention is easy to generate. Based on these, the invention is completed.

Specifically, the present inventors utilized human-derived IL-4 antigen protein to immunize camels to obtain a high-quality immune single-domain antibody gene library. Then the IL-4R protein molecule was coupled to the ELISA plate to display the correct spatial structure of IL-4R protein and was used as an antigen to screen the immune single domain antibody gene library (camel heavy chain antibody phage display gene library) via phage display technology, thereby obtaining the IL-4R specific single-domain antibody gene. The gene was then transferred into mammalian cells to obtain a single domain antibody strain that could be efficiently expressed in mammalian cells and had high specificity. Thereafter, the anti-IL-4R single-domain antibody with blocking activity was identified by ELISA, flow cytometry and luciferase reporter gene detection system, etc.

Terms

As used herein, the terms "single-domain antibody of the present invention", "anti-IL-4R single-domain antibody of the present invention", "IL-4R single-domain antibody of the present invention", "anti-IL-4R single-domain antibody", and "IL-4R single-domain antibody" have the same meaning and can be used interchangeably, and each refers to a single-domain antibody that specifically recognize and bind to IL-4R (including human IL-4R). Preferably, the variable region of the single-domain antibody of the present invention has CDR1 as shown in SEQ ID NO: 1, CDR2 as shown in SEQ ID NO: 2, and CDR3 as shown in SEQ ID NO: 3. More preferably, the framework region of the single-domain antibody of the present invention has (a) FR1 as shown in SEQ ID NO: 4, FR2 as shown in SEQ ID NO: 5, FR3 as shown in SEQ ID NO: 6, and FR4 as shown in SEQ ID NO: 7; or (b) FR1 as shown in SEQ ID NO: 10, FR2 as shown in SEQ ID NO: 11, FR3 as shown in SEQ ID NO: 12, and FR4 as shown in SEQ ID NO: 13.

As used herein, the term "antibody" or "immunoglobulin" is a heterotetrameric glycoprotein of about 150,000 Daltons with the same structural characteristics, which consists of two identical light chains (L) and two identical heavy chains (H). Each light chain is connected to the heavy chain through a covalent disulfide bond, and the number of disulfide bonds between heavy chains of different immunoglobulin isotypes is different. Each heavy and light chain also has regularly spaced disulfide bonds in the chain. Each heavy chain has a variable region (VH) at one end, followed by multiple constant regions. Each light chain has a variable region (VL) at one end and a constant region at the other end. The constant region of the light chain is opposite to the first constant region of the heavy chain, and the variable region of the light chain is opposite to the variable region of the heavy chain. Special amino acid residues form an interface between the variable regions of the light chain and the heavy chain.

As used herein, the terms "single-domain antibody", "VHH", "nanobody", "single domain antibody" (sdAb, or nanobody) have the same meaning and can be used interchangeably, and refer to a single domain antibody (VHH) consisting of only one heavy chain variable region, which is the smallest antigen-binding fragment with complete functions, wherein the VHH is constructed via cloning of the variable region of an antibody heavy chain. Usually, the antibody that naturally lacks the light chain and the heavy chain constant region 1 (CH1) is obtained, and then the variable region of the antibody heavy chain is cloned to construct a single domain antibody (VHH) consisting of only one heavy chain variable region.

As used herein, the term "variable" means that certain parts of the variable region in an antibody differ in sequence, which forms the binding and specificity of various specific antibodies for their specific antigens. However, the variability is not evenly distributed throughout the variable region of the antibody. It is concentrated in three segments called complementarity determining regions (CDRs) or hypervariable regions in the light chain variable regions and heavy chain variable regions. The more conserved part of the variable region is called the framework region (FR). The variable regions in the natural heavy and light chains each contain four FR regions, which are roughly in the β-fold configuration, connected by the three CDRs that form the connecting loop, and in some cases part of the β-folded structure may be formed. The CDRs in each chain are closely together through the FR region and together with the CDRs of the other chain to form the antigen-binding site of the antibody (see Kabat et al., NIH Publ. No. 91-3242, Volume I, pages 647-669) (1991)). The constant regions are not directly involved in the binding of antibodies to antigens, but they exhibit different effector functions, such as antibody-dependent cytotoxicity involved in antibodies.

As known to those skilled in the art, immunoconjugates and fusion expression products include: conjugates formed by combining drugs, toxins, cytokines, radionuclides, enzymes, and other diagnostic or therapeutic molecules with the antibodies or fragments thereof of the present invention. The present invention also includes cell surface markers or antigens that bind to the anti-IL-4R antibody or fragments thereof.

As used herein, the terms "heavy chain variable region" and "VH" can be used interchangeably.

As used herein, the terms "variable region" and "complementarity determining region (CDR)" can be used interchangeably.

In a preferred embodiment of the present invention, the heavy chain variable region of the antibody includes three complementarity determining regions CDR1, CDR2, and CDR3.

In a preferred embodiment of the present invention, the heavy chain of the antibody includes the above heavy chain variable region and heavy chain constant region.

In the present invention, the terms "antibody of the present invention", "protein of the present invention", or "polypeptide of the present invention" can be used interchangeably, and refer to a polypeptide that specifically binds to the IL-4R protein, such as a protein or polypeptide having a heavy chain variable region. They may or may not contain an initial methionine.

The present invention further provides other proteins or fusion expression products comprising the antibodies of the present invention. Specifically, the present invention includes any protein or protein conjugate and fusion expression product having a heavy chain containing a variable region (i.e., immunoconjugate and fusion expression product), as long as the variable region is the same as the heavy chain variable region of the antibody of the present invention or has at least 90% homology with that, preferably at least 95% homology with that.

In general, the antigen-binding properties of antibodies can be described by three specific regions located in the variable region of the heavy chain, called variable regions (CDRs). The segment is divided into 4 framework regions (FRs), the amino acid sequences of the four FRs are relatively conservative, and do not directly participate in the binding reaction. These CDRs form a circular structure, and the β-pleated sheet formed by the FRs in between are close to each other in space structure. The CDRs on the heavy chain and the CDRs on the corresponding light chain constitute the antigen binding site of the antibody. The amino acid sequences of antibodies of the same type can be compared to determine which amino acids constitute the FR or CDR regions.

The variable regions of the heavy chains of the antibodies of the present invention are of particular interest because at least parts of them are involved in binding antigens. Therefore, the present invention includes those molecules having a CDRs-containing antibody heavy chain variable region, as long as their CDRs have more than 90% (preferably more than 95%, most preferably more than 98%) homology with the CDRs identified herein.

The present invention includes not only whole antibodies, but also fragments of antibodies with immunological activity or fusion proteins formed by antibodies and other sequences. Therefore, the present invention also includes fragments, derivatives and analogs of the antibodies.

As used herein, the terms "fragment", "derivative" and "analog" refer to a polypeptide that substantially retains the same biological function or activity of the antibody of the present invention. The polypeptide fragment, derivative or analog of the present invention may be (i) a polypeptide having one or more conservative or non-conservative amino acid residues (preferably conservative amino acid residues) substituted, and such substituted amino acid residues may or may not be encoded by the genetic code, or (ii) a polypeptide with a substitution group in one or more amino acid residues, or (iii) a polypeptide formed by the fusion of a mature polypeptide with another compound (such as a compound that extends the half-life of the polypeptide, such as polyethylene glycol), or (iv) a polypeptide formed by fusing the additional amino acid sequence to the polypeptide sequence (such as a leader sequence or secretion sequence or a sequence or proprotein sequence used to purify the polypeptide, or a fusion protein formed with a 6His tag). According to the teachings herein, these fragments, derivatives and analogs are within the scope well known to those skilled in the art.

The antibody of the present invention refers to a polypeptide having IL-4R protein binding activity and containing the above-mentioned CDR regions. The term also includes variant forms of polypeptides containing the above CDR regions that have the same function as the antibodies of the present invention. These variant forms include (but are not limited to): one or more (usually 1-50, preferably 1-30, more preferably 1-20, most preferably 1-10) amino acid deletions, insertions and/or substitutions, and one or several (usually less than 20, preferably less than 10, and more preferably less than 5) amino acids addition to the C-terminal and/or N-terminal. For example, in the art, the substitution of amino acids with close or similar properties usually does not change the function of the protein. As another example, adding one or several amino acids to the C-terminus and/or N-terminus usually does not change the function of the protein. The term also includes active fragments and active derivatives of the antibodies of the present invention.

The variant forms of the polypeptide include: homologous sequences, conservative variants, allelic variants, natural mutants, induced mutants, proteins encoded by DNA that can hybridize with DNA encoding the antibody of the present invention under highly or lowly stringent conditions, and polypeptides or proteins obtained using antiserum against antibodies of the present invention.

The present invention further provides other polypeptides, such as fusion proteins comprising single-domain antibodies or fragments thereof. In addition to almost full-length polypeptides, the present invention also includes fragments of single-domain antibodies of the present invention. Generally, the fragment has at least about 50 consecutive amino acids, preferably at least about 50 consecutive amino acids, more preferably at least about 80 consecutive amino acids, and most preferably at least about 100 consecutive amino acids of the antibody of the present invention.

In the present invention, "conservative variant of the antibody of the present invention" refers to that compared with the amino acid sequence of the antibody of the present invention, at most 10, preferably at most 8, more preferably at most 5, and most preferably at most 3 amino acids are replaced by amino acids with similar or close properties to form a polypeptide. These conservative variant polypeptides are best produced by amino acid substitution according to Table 1.

TABLE 1

| The initial residues | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |

TABLE 1-continued

| The initial residues | Representative substitution | Preferred substitution |
|---|---|---|
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention further provides polynucleotide molecules encoding the above antibodies or fragments thereof. The polynucleotide of the present invention may be in the form of DNA or RNA. DNA forms include cDNA, genomic DNA, or synthetic DNA. DNA may be single-stranded or double-stranded. DNA may be a coding strand or a non-coding strand.

The polynucleotide encoding the mature polypeptide of the present invention includes: a coding sequence encoding only the mature polypeptide; a coding sequence encoding the mature polypeptide with various additional coding sequences; a coding sequence encoding the mature polypeptide (and optional additional coding sequences) and a non-coding sequence.

The term "polynucleotide encoding a polypeptide" may include a polynucleotide encoding the polypeptide, or a polynucleotide further containing additional coding and/or non-coding sequences.

The present invention also relates to polynucleotides that hybridize to the above-mentioned sequences and have at least 50%, preferably at least 70%, and more preferably at least 80% identity to the above-mentioned sequences. The present invention particularly relates to polynucleotides that can hybridize to the polynucleotides of the present invention under stringent conditions. In the present invention, "stringent conditions" means: (1) hybridization and elution at lower ionic strength and higher temperature, such as 0.2× SSC, 0.1% SDS, 60° C.; or (2) denaturing agent, such as 50% (v/v) formamide, 0.1% calf serum/0.1% Ficoll, 42° C., etc. is added during hybridization; or (3) hybridization occurs only when the identity between the two sequences is at least 90%, and more preferably at least 95%. Furthermore, the polypeptide encoded by the hybridizable polynucleotide has the same biological function and activity as the mature polypeptide.

The full-length nucleotide sequence of the antibody of the present invention or a fragment thereof can generally be obtained by PCR amplification method, recombination method or artificial synthesis method. A feasible method is to use synthetic methods to synthesize the relevant sequences, especially when the fragment length is short. Generally, a fragment with a very long sequence can be obtained by synthesizing multiple small fragments and then connecting them. In addition, the coding sequence of the heavy chain and the expression tag (such as 6His) can also be fused together to form a fusion protein.

Once the relevant sequence is obtained, the relevant sequence can be obtained in large quantities by the recombination method. This is usually done by cloning it into a vector, then transferring it into a cell, and then isolating the relevant sequence from the propagated host cell by conventional methods. The biomolecules (nucleic acids, proteins, etc.) involved in the present invention include biomolecules that exist in an isolated form.

At present, the DNA sequence encoding the protein (or a fragment or a derivative thereof) of the present invention can be obtained completely by chemical synthesis. This DNA sequence can then be introduced into various existing DNA molecules (or vectors) and cells known in the art. In addition, mutations can also be introduced into the protein sequence of the present invention by chemical synthesis.

The present invention also relates to vectors containing the appropriate DNA sequence as described above and an appropriate promoter or control sequence. These vectors can be used to transform appropriate host cells so that they can express proteins.

The host cell may be a prokaryotic cell, such as a bacterial cell; or a lower eukaryotic cell, such as a yeast cell; or a higher eukaryotic cell, such as a mammalian cell. Representative examples are: *Escherichia coli, Streptomyces*; bacterial cells of *Salmonella typhimurium*; fungal cells such as yeast; insect cells of *Drosophila* S2 or Sf9; animal cells of CHO, COS7, 293 cells, etc.

Transformation of host cells with recombinant DNA can be performed using conventional techniques well known to those skilled in the art. When the host is a prokaryotic organism such as *E. coli*, competent cells that can absorb DNA can be harvested after the exponential growth phase and treated with the $CaCl_2$) method. The procedures used are well known in the art. Another method is to use $MgCl_2$. If necessary, transformation can also be carried out by electroporation. When the host is a eukaryote, the following DNA transfection methods can be used: calcium phosphate co-precipitation method, conventional mechanical methods such as microinjection, electroporation, liposome packaging, etc.

The obtained transformant can be cultured by a conventional method to express the polypeptide encoded by the gene of the present invention. Depending on the host cell used, the medium used in the culture can be selected from various conventional mediums. The cultivation is carried out under conditions suitable for the growth of host cells. When the host cells grow to an appropriate cell density, the selected promoter is induced by an appropriate method (such as temperature conversion or chemical induction), and the cells are cultured for a period of time.

The recombinant polypeptide in the above method may be expressed in a cell or on a cell membrane, or secreted out of the cell. If necessary, the recombinant protein can be isolated and purified by various separation methods using its physical, chemical and other characteristics. These methods are well known to those skilled in the art. Examples of these methods include, but are not limited to: conventional renaturation treatment, treatment with protein precipitation agent (salting out method), centrifugation, disruption of bacteria through penetration, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

The antibody of the present invention may be used alone, or may be combined or coupled with a detectable label (for diagnostic purposes), a therapeutic agent, a PK (protein kinase) modified portion, or a combination or coupling of any of above these substances.

Detectable labels for diagnostic purposes include, but are not limited to: fluorescent or luminescent labels, radioactive labels, MRI (magnetic resonance imaging) or CT (electronic computer X-ray tomography) contrast agents, or an enzyme capable of producing a detectable product.

Therapeutic agents that can be combined or conjugated with the antibodies of the present invention include, but are not limited to: 1. radionuclides; 2. biotoxin; 3. cytokines such as IL-2, etc.; 4. gold nanoparticles/nanorods; 5. viral particles; 6. liposomes; 7. magnetic nanosphere; 8. prodrug-activating enzymes (e.g., DT-diaphorase (DTD) or biphenylhydrolase-like protein (BPHL)), etc.

Interleukin-4 (IL-4)

Interleukin-4 (IL-4, also known as B cells stimulating factor or BSF-1) is a cytokine mainly produced by activated T cells, monocytes, basophils, mast cells, and eosinophils. IL-4 can respond to low concentration of antibodies against the surface immunoglobulin and stimulate the proliferation of B cells. IL-4 has been shown to have a wide range of biological activities, including stimulating the growth of T cells, mast cells, granulocytes, megakaryocytes, and erythrocytes. IL-4 induces the expression of class II major histocompatibility complex molecules in resting B cells and enhances the secretion of IgE and IgG1 isotypes in stimulated B cells.

Interleukin-4 Receptor α (IL-4Rα)

The human IL-4Rα subunit is a 140 kDa type I membrane protein that binds human IL-4 with high affinity. Il-4Rα is expressed in low quantities in many cell types, such as peripheral blood T cells, monocytes, airway epithelial cells, B cells, and lung fibroblasts. Interleukin-4 receptor α subunit (IL-4Rα) locates in chromosome 16P12.1-PI1.2 region, which is also an asthma susceptibility region. Gene polymorphisms in this region are associated with hypersensitivity and elevated serum IgE levels. In addition, IL-4Rα is a common component of the IL-4 and IL-13 gene receptor complex. Studies have shown that IL-4Rα gene polymorphisms are associated with asthma, elevated serum IgE levels, and atopic dermatitis.

Pharmaceutical Composition

The present invention further provides a composition. Preferably, the composition is a pharmaceutical composition, which contains the above antibody or an active fragment thereof or fusion protein thereof, and a pharmaceutically acceptable carrier. Generally, these substances can be formulated in a non-toxic, inert and pharmaceutically acceptable aqueous carrier medium, wherein the pH is usually about 5-8, preferably about 6-8, although the pH may vary depending on the nature of the substance being formulated and the condition to be treated. The formulated pharmaceutical composition can be administered by conventional routes, including (but not limited to): intraperitoneal, intravenous, or topical administration.

The pharmaceutical composition of the present invention can be directly used to bind IL-4R protein molecules, and thus can be used to treat asthma, atopic dermatitis, arthritis, allergic rhinitis, eczema, etc. In addition, other therapeutic agents can be used simultaneously.

The pharmaceutical composition of the present invention contains a safe and effective amount (such as 0.001-99 wt %, preferably 0.01-90 wt %, more preferably 0.1-80 wt %) of the above single domain antibody (or its conjugate) of the present invention and a pharmaceutically acceptable carrier or excipient. Such carriers include (but are not limited to): saline, buffer, glucose, water, glycerin, ethanol, and a combination thereof. The pharmaceutical preparation should match the mode of administration. The pharmaceutical composition of the present invention can be prepared in the form of an injection, for example, prepared by a conventional method using a physiological saline or an aqueous solution containing glucose and other adjuvants. Pharmaceutical compositions such as injections and solutions are preferably manufactured under sterile conditions. The amount of active ingredient administered is a therapeutically effective amount, for example, about 10 micrograms/kg body weight to about 50 mg/kg body weight per day. In addition, the polypeptide of the present invention can be used together with other therapeutic agents.

When using a pharmaceutical composition, a safe and effective amount of an immunoconjugate is administered to a mammal, wherein the safe and effective amount is usually at least about 10 µg/kg body weight, and in most cases does not exceed about 50 mg/kg body weight, preferably the dose is about from 10 µg/kg body weight to about 10 mg/kg body weight. Of course, the specific dosage should also consider factors such as the route of administration, the patient's health status, etc., which are within the skills of skilled physicians.

Anti-IL-4R Single-Domain Antibody

In the present invention, the anti-IL-4R single-domain antibody includes monomer, bivalent antibody, tetravalent antibody, and/or multivalent antibody.

In a preferred embodiment of the present invention, the anti-IL-4R single-domain antibody comprises one, two or more VHH chains of amino acid sequence as shown in SEQ ID NO: 8 and/or SEQ ID NO: 14.

Typically, the anti-IL-4R single-domain antibody comprises two VHH chains of amino acid sequence as shown in SEQ ID NO: 8 and/or SEQ ID NO: 14.

In another preferred embodiment, the anti-IL-4R single-domain antibody comprises four VHH chains of amino acid sequence as shown in SEQ ID NO: 8 and/or SEQ ID NO: 14.

Typically, the anti-IL-4R single-domain antibody comprises VHH chains of amino acid sequence as shown in SEQ ID NO: 8 and/or SEQ ID NO: 14.

Typically, the anti-IL-4R single-domain antibody comprises two VHH chains of amino acid sequence as shown in SEQ ID NO: 14.

Typically, the anti-IL-4R single-domain antibody comprises four VHH chains of amino acid sequence as shown in SEQ ID NO: 14.

In a preferred embodiment of the present invention, the two VHH chains containing amino acid sequence as shown in SEQ ID NO: 8 are linked via a linker.

In a preferred embodiment of the present invention, the two VHH chains containing amino acid sequence as shown in SEQ ID NO: 14 are linked via linkers.

In a preferred embodiment of the present invention, the linker is selected from the following sequences: $(G_aS_b)_x$-$(G_mS_n)_y$, wherein each of a, b, m, n, x, and y is 0 or 1 or 1 or 2 or 3 or 4 or 5 or 6 or 7 or 8 or 9 or 10 (more preferably, a=4, while b=1, and m=3 while n=1).

In a preferred embodiment of the present invention, the linker is selected from the group consisting of GGGGSGGGS (SEQ ID NO: 18).

In a preferred embodiment of the present invention, the amino acid sequence of the bivalent anti-IL-4R single-domain antibody is shown as SEQ ID NO: 16.

In a preferred embodiment of the present invention, the bivalent anti-IL-4R single-domain antibody is shown as SEQ ID NO: 19.

Labeled Single-Domain Antibody

In a preferred embodiment of the present invention, the single-domain antibody has a detectable label. More preferably, the label is selected from the group consisting of: isotopes, colloidal gold labels, colored labels or fluorescent labels.

Colloidal gold labeling can be performed using methods known to those skilled in the art. In a preferred embodiment of the present invention, the anti-IL-4R single-domain antibody is labeled with colloidal gold to obtain a colloidal gold labeled single-domain antibody.

The new anti-IL-4R single-domain antibody of the present invention has good specificity and high titer.

Detection Method

The present invention further relates to a method for detecting IL-4R protein. The steps of the method are roughly as follows: obtaining a cell and/or tissue sample; dissolving the sample in a medium; and detecting the level of IL-4R protein in the dissolved sample.

In the detection method of the present invention, the sample used is not particularly limited, and a representative example is a cell-containing sample present in a cell preservation solution.

Kit

The present invention further provides a kit containing the antibody (or a fragment thereof) or a detection plate of the present invention. In a preferred embodiment of the present invention, the kit further includes a container, an instruction for use, a buffer, and the like.

The present invention further provides a detection kit for detecting the level of IL-4R, which includes an antibody that recognizes the IL-4R protein, a lysis medium for dissolving the sample, general reagents and buffers required for the detection, such as various buffers, detection markers, detection substrates, etc. The detection kit may be an in vitro diagnostic device.

Application

As described above, the single-domain antibody of the present invention has a wide range of biological application value and clinical application value, and its application involves the diagnosis and treatment of IL-4R-related diseases, basic medical research, biological research and other fields. A preferred application is for clinical diagnosis and targeted therapy for IL-4R.

The main advantages of the present invention include:
(a) The single-domain antibody of the present invention specifically binds to IL-4R protein with correct spatial structure.
(b) The single-domain antibody of the present invention can recognize the human and marmoset IL-4R, but not mouse IL-4R.
(c) The single-domain antibody of the present invention has a stronger binding and blocking activity than that of the commercially available monoclonal antibody Dupilumab.
(d) The single-domain antibody of the present invention has a good inhibitory effect on the proliferation of TF-1 cell, which is superior to that of the commercially available monoclonal antibody Dupilumab.
(e) The single-domain antibody of the present invention can effectively inhibit the activation of pSTAT6 signal pathway in cells, which is superior to that of the commercially available monoclonal antibody Dupilumab.
(f) The production of the single-domain antibody of the present invention is simple.

The invention will be further illustrated with reference to the following specific examples. It is to be understood that these examples are only intended to illustrate the invention, but not to limit the scope of the invention. For the experimental methods in the following examples without particular conditions, they are performed under routine conditions (e.g. Sambrook et al., Molecular Cloning: A Laboratory Manual (third edition) (2001, CSHL Press) or as instructed by the manufacturer. Unless otherwise specified, all percentages or parts are by weight.

Example 1: Screening and Expression of Anti-IL-4R Single-Domain Antibody

Figure 2:
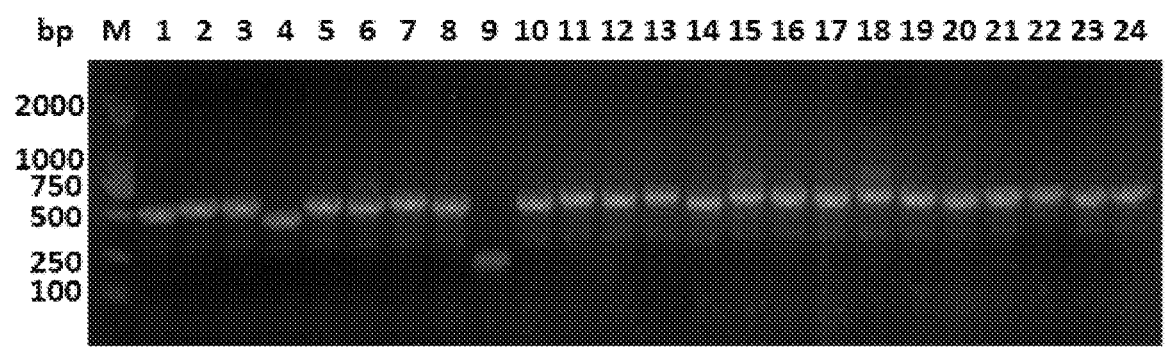
FIG. 2 shows the fragment insertion rate of the phage display IL-4R single-domain antibody library. The monoclonal antibodies in the library were randomly selected for PCR detection, and the calculated insertion rate of monoclonal library is 95.8%.

In order to obtain a single-domain antibody specific for human IL-4R, firstly, human IL-4R protein was transiently expressed by a mammalian cell HEK293F, and then used for immunization in a camel after affinity purification. For specific methods, please refer to the method described in Example 1 and Example 2 of the patent CN2018101517526. Briefly, one Xinjiang Bactrian camel was immunized with purified IL-4R protein. Total RNA was isolated from camel peripheral blood after 7 times of immunization. Then VHH gene was amplified by reverse transcription and PCR, and cloned into phage vector pMECS, and transformed into TG1 to construct the phage display library. The capacity of the constructed library capacity is $1.1 \times 10^9$ CFU as shown in FIG. 1, and the library insertion rate is 95.8% as shown in FIG. 2. Subsequently, the library was screened by 3 rounds of screening to obtain enriched phages containing antibody genes. 300 clones were selected from the library for PE-ELISA identification, and the obtained positive clones were sequenced, and then the single-domain antibodies with different sequences were transiently expressed by E. coli system. The expression method was described in Example 4 of patent CN2018101517526.

Figure 3:
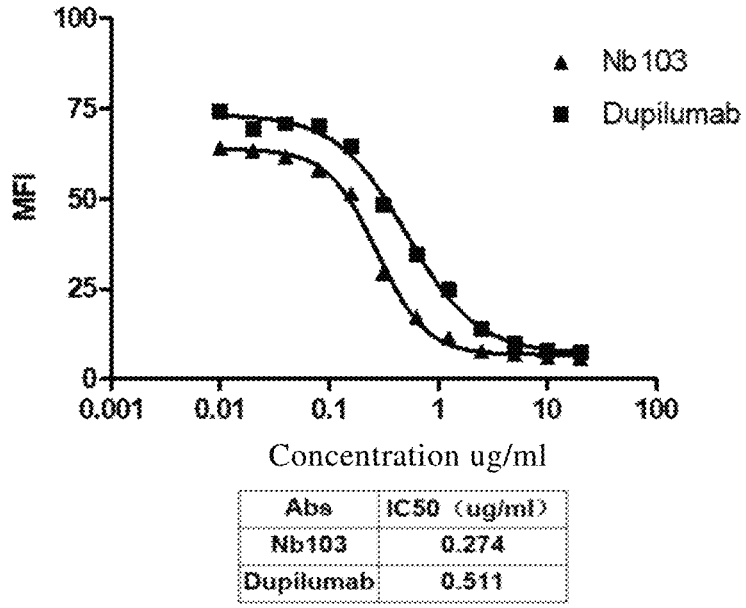
FIG. 3 shows the blocking activity of a blocking IL-4R single-domain antibody identified by flow cytometry. The blocking activity of IL-4R single-domain antibody Nb103 was superior to that of the control antibody Dupilumab ($IC_{50\ Nb103}$=0.274 ug/mL, $IC_{50\ Dupilumab}$=0.511 ug/mL).

Example 2: Screening of Anti-IL-4R Single-Domain Antibody with Blocking Activity by FACS (1) A certain number of 293F/IL-4R cells that were transitioned for 48 h were centrifuged at 1000 rpm for 5 min, the supernatant was discarded, the cells were re-suspended and washed with PBS for once, and counted. The cells were divided into 96-well plates at 100 ul/well, and then centrifuged at 3000 rpm at 4° C. for 4 min. (2) The supernatant was aspirated, and the single-domain antibody with different sequences in gradient diluted in example 1 was added (two-fold gradient dilution starting from 40 ug/mL). 50 uL was added to each well, and then 50 uL of 5 ug/mL IL-4-biotin was added to mix, and incubated at 4° C. for 20 min. (3) Centrifugation was performed at 3000 rpm at 4° C. for 4 min, and the supernatant was discarded. 200 uL PBS was added to each well to wash the cells, and the supernatant was discarded by centrifugation again. Diluted SA-PE staining solution was added and incubated at 4° C. for 20 min. (4) Centrifugation was performed at 3000 rpm at 4° C. for 4 min, and the supernatant was discarded. 200 uL PBS was added to each well to wash the cells, and the supernatant was discarded by centrifugation again. 200 uL PBS was added to re-suspend the cells, and the PE signal of the samples was detected by flow cytometry. The results are shown in FIG. 3. A candidate single-domain IL-4R antibody Nb103 ($IC_{50\ Nb103}$=0.274 ug/mL) with good blocking activity was obtained, which was superior to that of the control antibody Dupilumab ($IC_{50\ Dupilumab}$=0.511 ug/mL).

Figure 4:
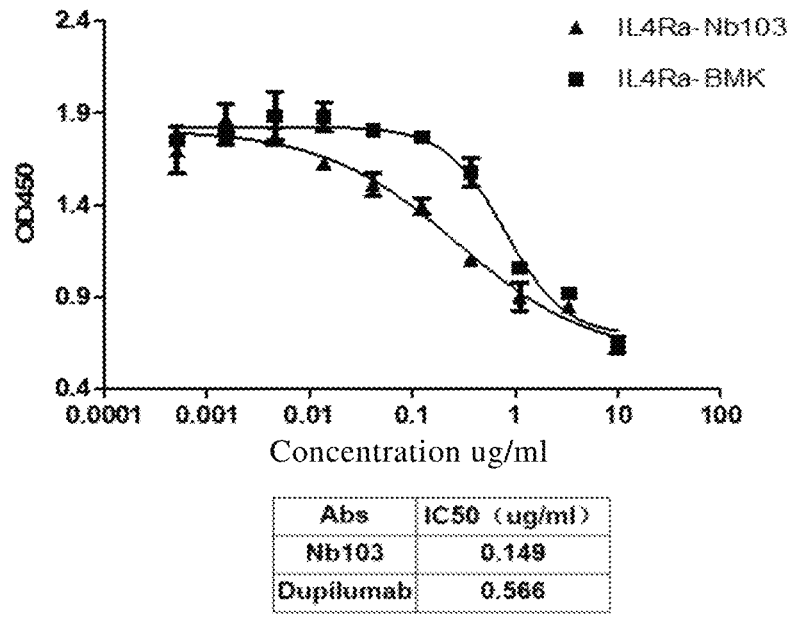
FIG. 4 shows the proliferation inhibition effect of blocking IL-4R single-domain antibody identified by flow cytometry on TF-1 cells induced by IL-4. The blocking activity of the candidate single-domain antibody Nb103 on TF-1 cells was significantly higher than that of the control antibody Dupilumab ($IC_{50\ Nb103}$=0.149 ug/mL, $IC_{50\ Dupilumab}$=0.566 ug/mL).

Example 3: The Proliferation Inhibitory Effect on the TF-1 Cell of the Candidate Single-Domain Antibody by FACS The detection method of the proliferation inhibitory effect on the TF-1 cell induced by IL-4 of the candidate single-domain antibody was as follows: (1) A certain number of TF-1 cells were taken, centrifuged at 1000 rpm for 5 min, and the supernatant was discarded. PBS was added to resuspend the cells, and the cells were centrifuged at 1000 rpm for 5 min and washed once. After that, an appropriate amount of PBS was added to resuspend and count the cells, and the concentration of the cell solution was diluted to $6 \times 10^5$/mL, and the cells were divided into 96-well plates. (2) 50 uL gradient diluted (three times gradient dilution starting from 20 ug/mL) IgG1 (negative control), Dupilumab (positive control) and IL-4Ra Nb103 antibody were mixed with 50 uL 200 ng/mL IL-4 protein, and the collected cells were resuspended. At the same time, 100 uL PBS was added to all wells around the cells to prevent evaporation of the solution in the wells containing cells. (4) The cells were cultured in the incubator for 3 days. After 3 days, the cells were taken out and added with CCK8 solution at 10 uL/well. The cells were placed at 37° C. for 4 h for developing. (5) After developing, the OD450 of each well was read with a microplate reader. The results are shown in FIG. 4: $IC_{50\ Nb103}$=0.149 ug/mL and $IC_{50\ Dupilumab}$=0.566 ug/mL. Therefore, the inhibitory effect of candidate single-domain antibody Nb103 on TF-1 cell proliferation is significantly stronger than that of control antibody Dupilumab.

Figure 5:
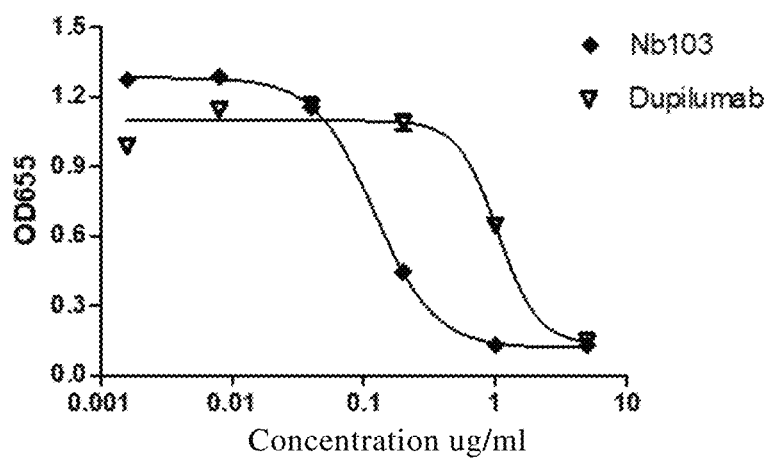
FIG. 5 shows the proliferation inhibition effect of the blocking IL-4R single-domain antibody identified by flow cytometry on TF-1 cells induced by IL-13. The blocking activity of the candidate single-domain antibody Nb103 on TF-1 cells was significantly higher than that of the control antibody Dupilumab ($IC_{50\ Nb103}$=0.066 ug/mL, $IC_{50\ Dupilumab}$=0.740 ug/mL).

The detection method of the inhibitory effect of candidate single-domain antibody on the proliferation of TF-1 cells induced by IL-13 was the same as above. The diluted antibody to be tested was mixed with IL-13 at a concentration of 10 ng/mL, and added into the cells. The results of detection are shown in FIG. 5: $IC_{50\ Nb103}$=0.066 ug/mL and $IC_{50\ Dupilumab}$=0.740 ug/mL. Therefore, the inhibitory effect of candidate single-domain antibody Nb103 on TF-1 cell proliferation is significantly stronger than that of control antibody Dupilumab.

Figure 6:
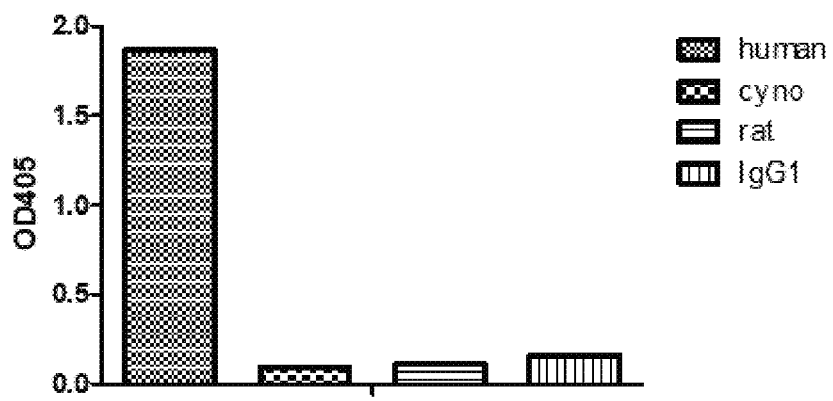
FIG. 6 shows the binding properties of IL-4R single-domain antibody Nb103 to different IL-4R species detected by ELISA. The candidate antibody Nb103 can recognize human IL-4R, but not mouse IL-4R and cynomolgus monkey IL-4R.

Example 4: The Species Specificity of Candidate Single-Domain Antibody Detected by ELISA ELISA was used to verify whether the candidate antibody could cross-react with IL-4R proteins of different species, and the method was as follows: (1) 1 ug/mL human IL-4R, mouse IL-4R and cynomolgus monkey IL-4R were added into the plate and coated overnight at 4° C. with 100 uL/well. (2) After washing with PBST for 5 times, 300 uL 1% BSA was added to each well and sealed for 2 hours at room temperature. (3) After washing with PBST for 5 times, 100 uL of 2 ug/mL antibody to be tested was added and incubated at 37° C. for 1 hour. (4) After washing with PBST for 5 times, 100 uL diluted anti-HA antibody (diluted at 1:2000) was added and incubated at 37° C. for 1 hour. (4) After washing with PBST for 5 times, 100 uL diluted anti-mouse IgG antibody (diluted at 1:2000) was added and incubated at 37° C. for 30 minutes. (5) After washing with PBST for 5 times, 100 uL PA chromogenic solution was added and developing at 37° C. for 10 minutes, and the absorption value was measured at 405 nm wavelength with a microplate reader. The results are shown in FIG. 6, the candidate antibody Nb103 can recognize the human IL-4R, but not mouse and cynomolgus monkey IL-4R.

Figure 7:
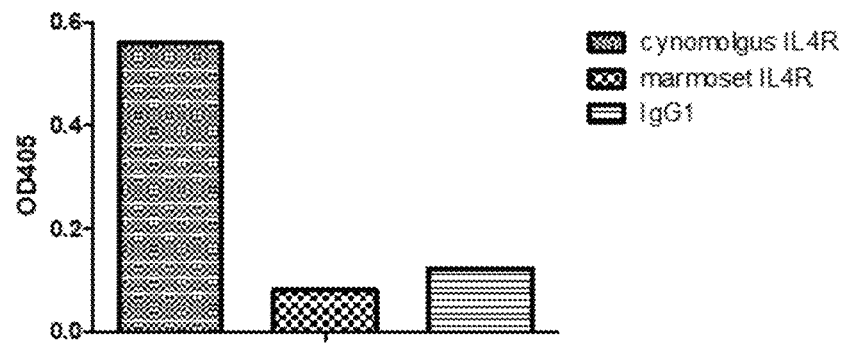
FIG. 7 shows the binding properties of IL-4R single-domain antibody Nb103 to different types of monkey IL-4R detected by ELISA. The candidate antibody Nb103 can recognize marmoset IL-4R, but not rhesus monkeys IL-4R.

ELISA was used again to verify whether the candidate antibody could cross-react with IL-4R protein of different monkey types. The detection method was the same as above. The results are shown in FIG. 7: the candidate antibody Nb103 can recognize the marmoset IL-4R, but not rhesus monkeys IL-4R.

Example 5: Humanization of Candidate Single-Domain Antibody

The candidate antibody was humanized wherein the variable region was kept unchanged, and humanized design was carried out for the sequence of the four framework regions. The huamanization method refers to the method of Example 4 in patent application CN2018101517526. Then, the humanized antibody sequence was constructed on pFUSE vector to fuse the humanized single-domain antibody with Fc sequence and to form huNb103 (the fusion protein sequence refers to SEQ ID NO:16, and the encoding nucleotide sequence thereof refers to SEQ ID NO:17), and expressed by HEK293F system. The expressed protein could be used for subsequent verification. The expression method refers to Example 3 in patent application CN2018101517526. The humanized antibody sequences are as shown in the following Table 2:

TABLE 2

| Antibody region | Sequence number (SEQ ID NO:) | |
|---|---|---|
| | Before humanization | After humanization |
| FR1 | 4 | 10 |
| CDR1 | 1 | 1 |
| FR2 | 5 | 11 |
| CDR2 | 2 | 2 |
| FR3 | 6 | 12 |
| CDR3 | 3 | 3 |
| FR4 | 7 | 13 |
| Complete amino acid sequence | 8 | 14 |
| Complete nucleotide sequence | 9 | 15 |

Example 6: Binding Activity of the Humanized Antibody Detected by FACS (1) HEK293F cells with high IL-4Rα expression were collected, centrifuged at 1000 rpm for 5 min, and the supernatant was discarded. The cells were re-suspended with 5 mL PBS and centrifuged at 1000 rpm for 5 min, and the supernatant was discarded. Then the cells were re-suspended with 2 mL PBS, and counted. The cells were divided into 96-well plates with $3 \times 10^5$ cells per well; (2) Humanized antibody huNb103 (amino acid sequence refers to SEQ ID NO:16) and Dupilumab were diluted by 2-fold gradient dilution (40 ug/mL, 20 ug/mL, 10 ug/mL, 5 ug/mL, 2.5 ug/mL, 1.25 ug/mL, 0.625 ug/mL, 0.313 ug/mL, 0.156 ug/mL, 0.078 ug/mL). The cells in the 96-well plate were resuspended with the diluted antibody and incubated at 4° C. for 20 min. (3) Centrifugation was performed at 3000 rpm at 4° C. for 4 min, and 200 ul PBS was added to each well. After resuspension, centrifugation was performed at 3000 rpm at 4° C. for 4 min. (4) Diluted anti-human Fc-FITC antibody (diluted at 1:200) was added and incubated at 4° C. for 20 min. (5) Centrifugation was performed at 3000 rpm at 4° C. for 4 min, and the supernatant was discarded, 200 uL PBS was added into each well to wash cells for two times, then 200 uL PBS was added to re-suspend the cells. The cells were transferred to flow tube to detect FITC signal of each sample via flow cytometry.

Figure 8:
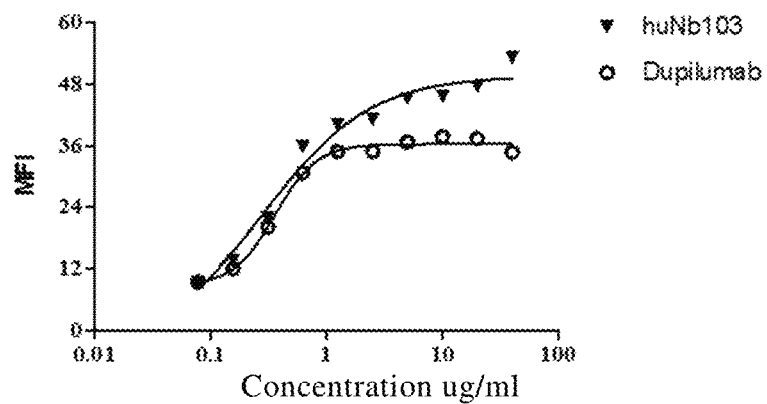
FIG. 8 shows the binding activity of humanized IL-4R single-domain antibody to human IL-4R detected by flow cytometry. The $EC_{50}$ of humanized antibody huNb103 is 0.286 ug/mL, and that of control antibody Dupilumab is 0.360 ug/mL.

The results are shown in FIG. 8. The $EC_{50}$ of the humanized antibody huNb103 is 0.286 ug/mL, and the $EC_{50}$ of the control antibody Dupilumab is 0.360 ug/mL.

Example 7: Blocking Activity of the Humanized Antibody Detected by FACS (1) HEK293F cells with high IL-4Rα expression were collected, centrifuged at 1000 rpm for 5 min, and the supernatant was discarded. The cells were re-suspended with 5 mL PBS and centrifuged at 1000 rpm for 5 min, and the supernatant was discarded. Then the cells were re-suspended with 2 mL PBS, and counted. The cells were divided into 96-well plates with $3\times10^5$ cells per well. (2) Humanized antibody huNb103 (amino acid sequence refers to SEQ ID NO:16) and Dupilumab were diluted by 2-foldgradient dilution (40 ug/mL, 20 ug/mL, 10 ug/mL, 5 ug/mL, 2.5 ug/mL, 1.25 ug/mL, 0.625 ug/mL, 0.313 ug/mL, 0.156 ug/mL, 0.078 ug/mL). The cells in the 96-well plate were resuspended with the diluted antibody and incubated at 4° C. for 20 min. (3) Centrifugation was performed at 3000 rpm at 4° C. for 4 min, and 200 ul PBS was added to each well. After resuspension, centrifugation was performed at 3000 rpm at 4° C. for 4 min. (4) Diluted SA-PE staining solution (diluted at 0.3:100) was added and incubated at 4° C. for 20 min. (5) Centrifugation was performed at 3000 rpm at 4° C. for 4 min, and the supernatant was discarded, 200 uL PBS was added into each well to wash cells for two times, then 200 uL PBS was added again to re-suspend the cells. The cells were transferred to flow tube to detect PE signal of each sample via flow cytometry.

Figure 9:
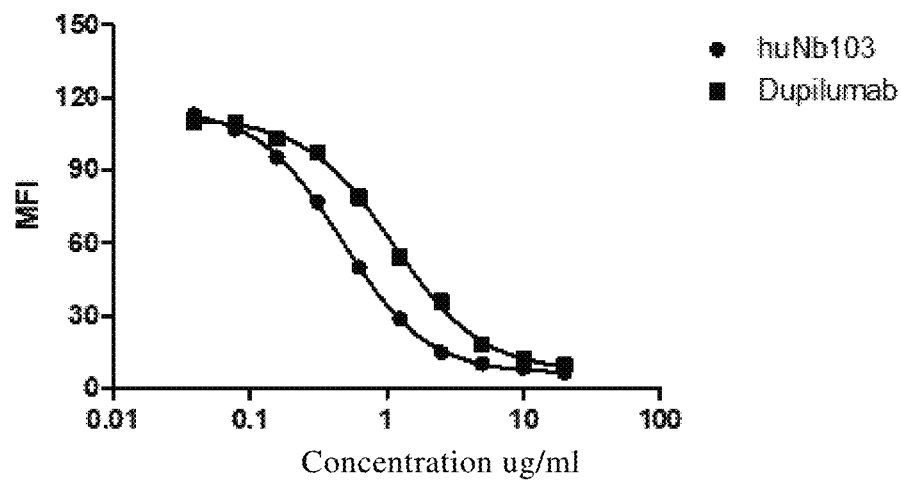
FIG. 9 shows the blocking activity of humanized IL-4R single-domain antibody to IL-4/IL-4R detected by flow cytometry. The $IC_{50}$ of humanized antibody huNb103 is 0.474 ug/mL, and that of control antibody Dupilumab is 1.126 ug/mL.

The results are shown in FIG. 9. The $IC_{50}$ of the humanized antibody huNb103 is 0.474 ug/mL, and the $IC_{50}$ of the control antibody Dupilumab is 1.126 ug/mL.

Example 8: Construction and Preparation of Humanized Tetravalent Antibody

Figure 10:
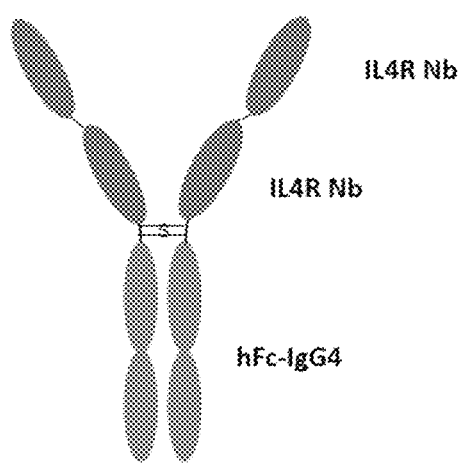
FIG. 10 shows a schematic diagram of humanized tetravalent antibodies.
Figure 11:
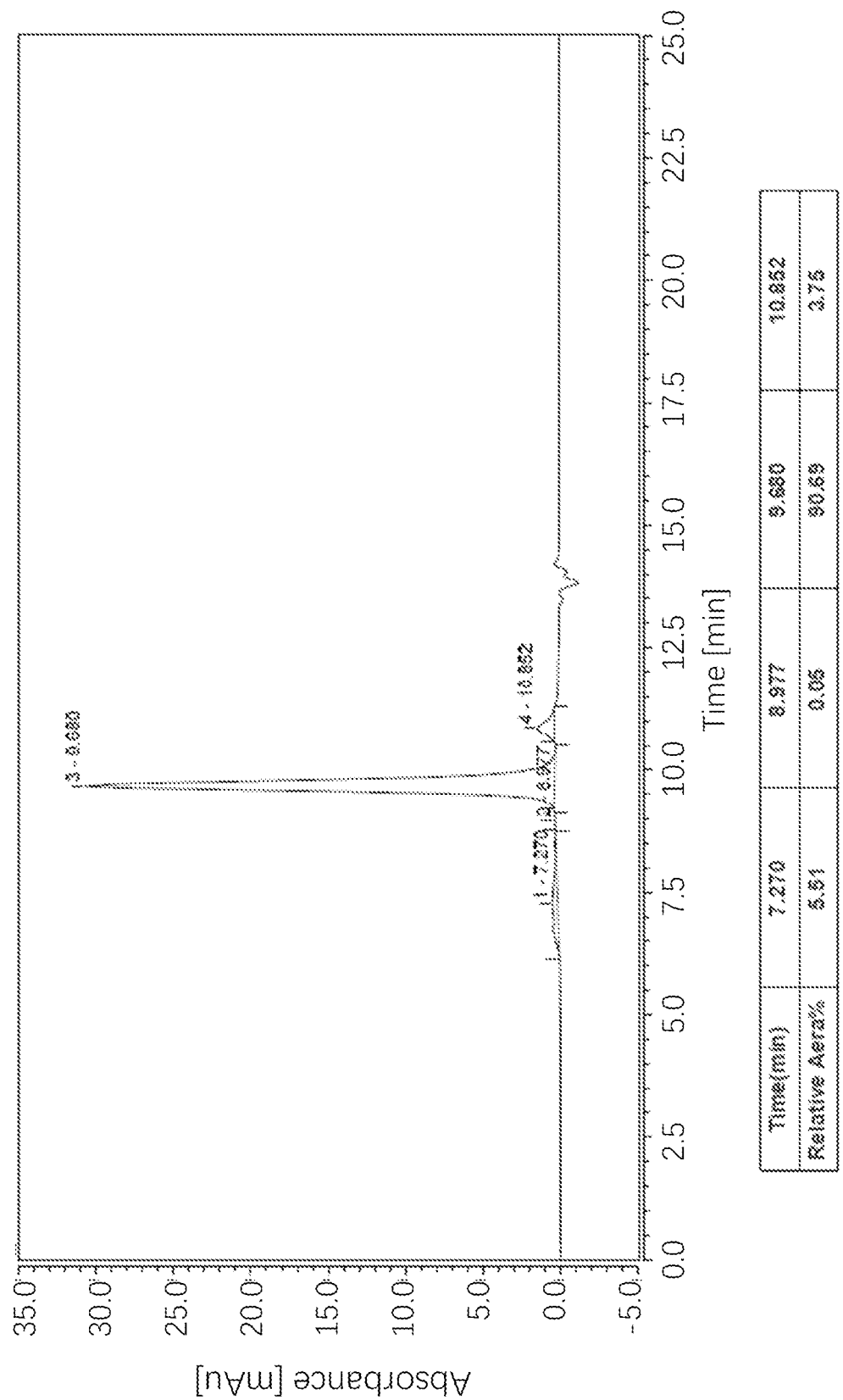
FIG. 11 shows the purity of humanized tetravalent antibodies identified by SEC-HPLC. The purity of the expressed humanized tetravalent antibody tet-huNb103 is 90.69%.

In order to further improve the activity of the antibody, the multivalent antibody was designed for preparation. The structure of the constructed tetravalent single-domain antibody is shown in FIG. 10, and the corresponding amino acid sequence is shown as SEQ ID NO:19, and the coding nucleotide sequence is SEQ ID NO:20. The nucleotide sequence containing the sequence as shown in SEQ ID NO:20 was synthesized into pCDNA3.1+ vector, and then the synthesized plasmid was transfected into HEK293F cells. The transfection method refers to Example 3 in patent application CN2018101517526. The purity of the expressed antibody was detected by SEC-HPLC, and the results were shown in FIG. 11. The purity of the antibody was 90.69%, which could be used for subsequent studies.

Example 9: Inhibitory Effect of Humanized Tetravalent Antibody on TF-1 Cell Proliferation (1) The resuscitated TF-1 cells were centrifuged at 1000 rpm for 5 min, and the supernatant was discarded. The cells were resuspended with 5 mL PBS, and centrifuged at 1000 rpm for 5 min. The cells were resuspended with 5 mL PBS and counted. The concentration of cell solution was diluted to $6\times10^5$/mL, and divided into a 96-well plate at 60 uL/well. (2) After 50 uL of IL-4Rα antibody in gradient dilution (50 ug/mL, 12.5 ug/mL, 3.125 ug/mL, 0.781 ug/mL, 0.195 ug/mL, 0.049 ug/mL, 0.012 ug/mL, 0.003 ug/mL) were mixed with 50 uL of 5 ng/mL IL-4 protein respectively, 40 uL of the each mixture was taken out and added to the cell solution. (3) At the same time, 200 uL PBS was added to all wells around the cells to prevent evaporation of the solution in the wells containing cells, and cultured at 37° C. in a 5% CO2 incubator for 72 h. (4) The cell culture plate was taken out, and added with 10 uL CCK8 solution to the wells, then placed at 37° C. for 4 h for developing. (5) After developing, OD450 value of each well was read with a microplate reader.

Figure 12:
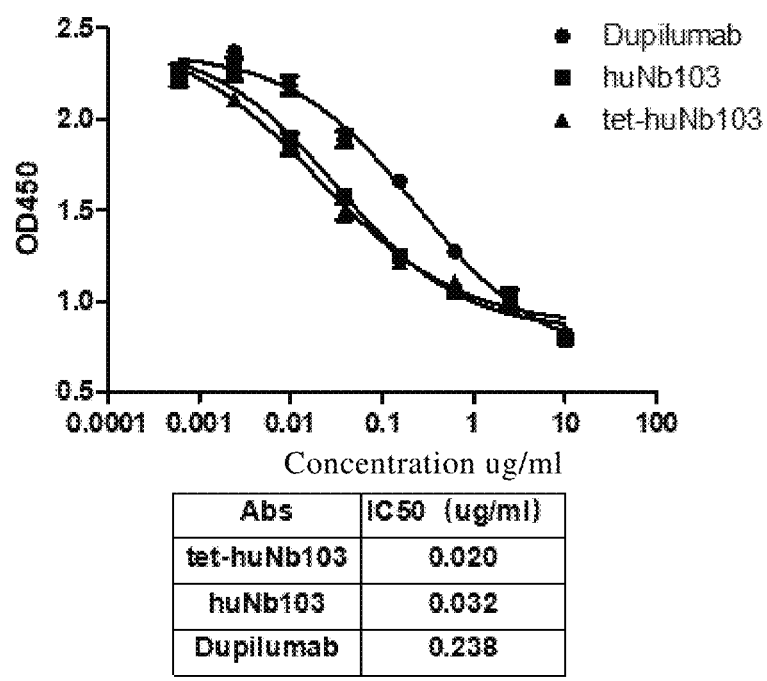
FIG. 12 shows the killing effect of humanized tetravalent antibody on TF-1 cells induced by IL-4. Humanized tetravalent antibodies could effectively inhibit the proliferation inhibitory on TF-1 cells induced by IL-4. The inhibitory activity $IC_{50\ tet-huNb103}$ is 0.020 ug/mL. Its activity is 1-2 times that of humanized bivalent antibody ($IC_{50\ huNb103}$=0.032 ug/mL), and is also significantly superior to that of the control antibody on TF-1 cells ($IC_{50\ Dupilumab}$=0.238 ug/mL).

The results are shown in FIG. 12: humanized tetravalent antibody can effectively inhibit the proliferation of the TF-1 cells induced by IL-4, and its inhibitory activity $IC_{50\ tet-huNb103}$ is 0.020 ug/mL. The activity is 1-2 times to that of the humanized bivalent antibody ($IC_{50\ huNb103}$=0.032 ug/mL), and is also significantly superior to the inhibitory effect on the proliferation of the TF-1 cells of the control antibody ($IC_{50\ Dupilumab}$=0.238 ug/mL).

Figure 13:
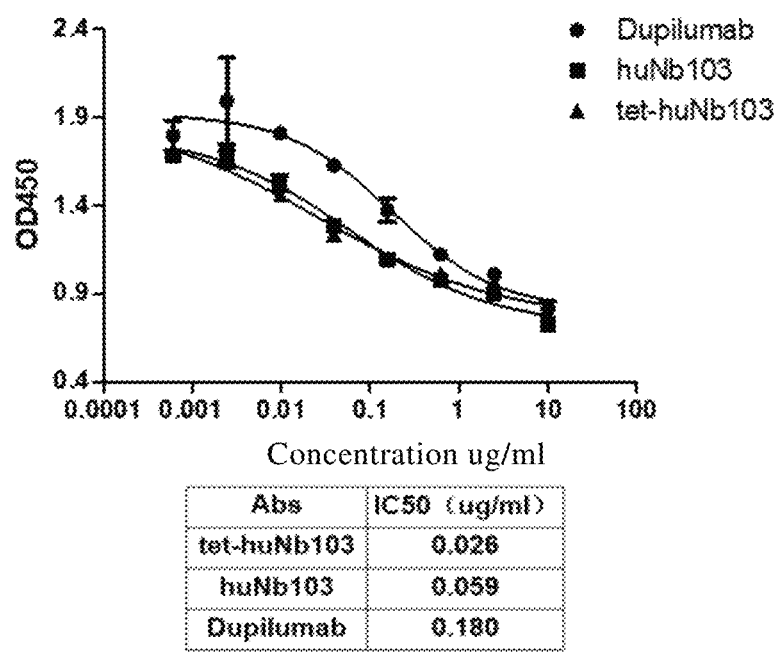
FIG. 13 shows the killing effect of humanized tetravalent antibody on TF-1 cells induced by IL-13. Humanized tetravalent antibodies could effectively inhibit the proliferation inhibitory on TF-1 cells induced by IL-13. The inhibitory activity $IC_{50\ tet-huNb103}$ is 0.026 ug/mL. Its activity is 2-3 times that of humanized bivalent antibody ($IC_{50\ huNb103}$=0.059 ug/mL), and is also significantly superior to that of the control antibody on TF-1 cells ($IC_{50\ Dupilumab}$=0.180 ug/mL).

Similarly, the inhibitory effect on the proliferation of TF-1 cells induced by IL-13 of the tetravalent antibody is also significant. The concentration of IL-13 added during detection was 10 ng/mL, and the other steps were the same as above. The results are shown in FIG. 13: humanized tetravalent antibody can effectively inhibit the proliferation of TF-1 cells induced by IL-13, and its inhibitory activity $IC_{50\ tet-huNb103}$ is 0.026 ug/mL. The activity is 2-3 times to that of human bivalent antibody ($IC_{50\ huNb103}$=0.059 ug/mL), and is also significantly superior to the inhibitory effect on the proliferation of the TF-1 cells of the control antibody ($IC_{50\ Dupilumab}$=0.180 ug/mL).

Example 10: Detection of the Inhibitory Effect of Humanized Tetravalent Antibody on pSTAT6 Signal Pathway in HEK-Blue™ IL-4/IL-13 Cells (1) HeK-IL-4/IL-13™ cells were cultured at 37° C. with 5% CO2. After growing to a certain number, the cells were collected, washed with 20 mL PBS twice, and then resuspended with 10 mL DMEM complete medium. 50 uL Trypan blue staining solution and 50 uL cell solution were mixed for cell counting. The concentration of HEK-IL-4/IL-13™ cell solution was diluted to $3\times10^5$/mL, and the cells were divided into a 96-well culture plate at 160 uL/well. (2) The antibody to be tested in gradient dilution (40 ug/mL, 10 ug/mL, 0.625 ug/mL, 0.156 ug/mL, 0.039 ug/mL, 0.010 ug/mL, 0.002 ug/mL) was mixed with an equal volume of 5 ng/mL IL-4 protein respectively. (3) 40 uL of the mixture was added to the packed cell plate, and 200 uL of PBS was added to the all wells around the cells to prevent evaporation of the solution in the wells containing cells. Incubation was performed at 37° C. in a 5% CO2 incubator for 22 h. (4) Quanti-Blue reagent was added to the 96-well plate, 180 uL/well, and then 20 uL cultured cell supernatant was added and incubated at 37° C. for 2 h. The reading value at 655 nm was detected by a microplate reader.

Figure 14:
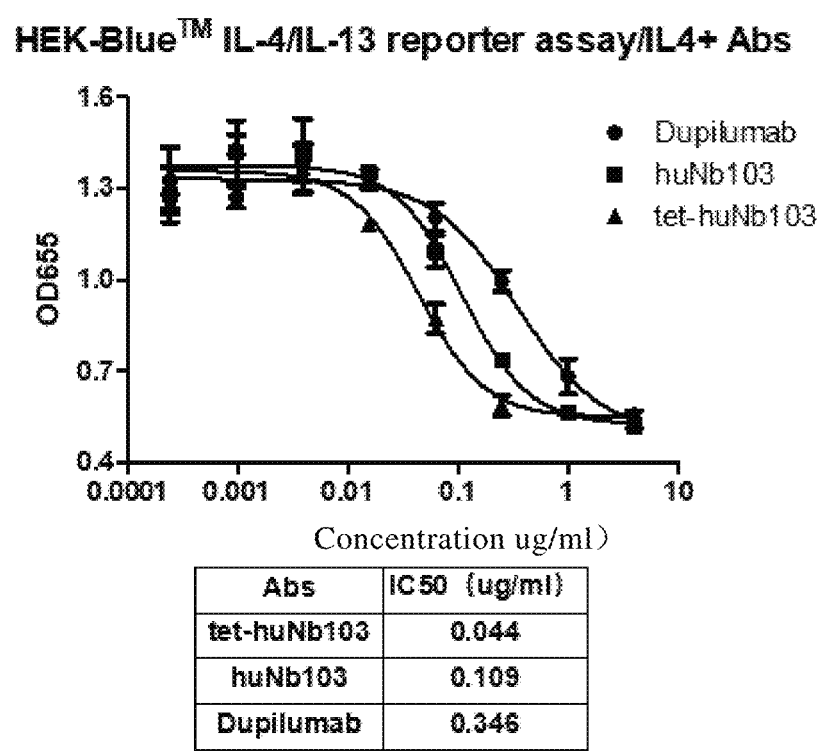
FIG. 14 shows the inhibitory effect of humanized tetravalent antibodies on the pSTAT6 signaling pathway in HEK-Blue™ IL-4/IL-13 cells induced by IL-4. Humanized tetravalent antibody can effectively inhibit the pSTAT6 signaling pathway of HEK-Blue™ IL-4/IL-13 cells induced by IL-4, with inhibitory activity $IC_{50\ tet-huNb103}$=0.044 ug/mL. Its activity is 2-3 times higher than that of humanized bivalent antibody ($IC_{50\ huNb103}$=0.109 ug/mL), and it is significantly superior to that of the control antibody on pSTAT6 signaling pathway (IC$_{50\ Dupilumab}$=0.346 ug/mL).

The results are shown in FIG. 14, humanized tetravalent antibody can effectively inhibit the pSTAT6 signal pathway in HeK-IL-4/IL-13™ cells induced by IL-4, and its inhibitory activity $IC_{50\ tet-huNb103}$ is 0.044 ug/mL. The activity is 2-3 times to that of the humanized bivalent antibody ($IC_{50\ huNb103}$=0.109 ug/mL), and is also significantly superior to the inhibitory effect on the pSTAT6 signal pathway in HeK-IL-4/IL-13™ cells of the control antibody ($IC_{50\ Dupilumab}$=0.346 ug/mL).

Figure 15:
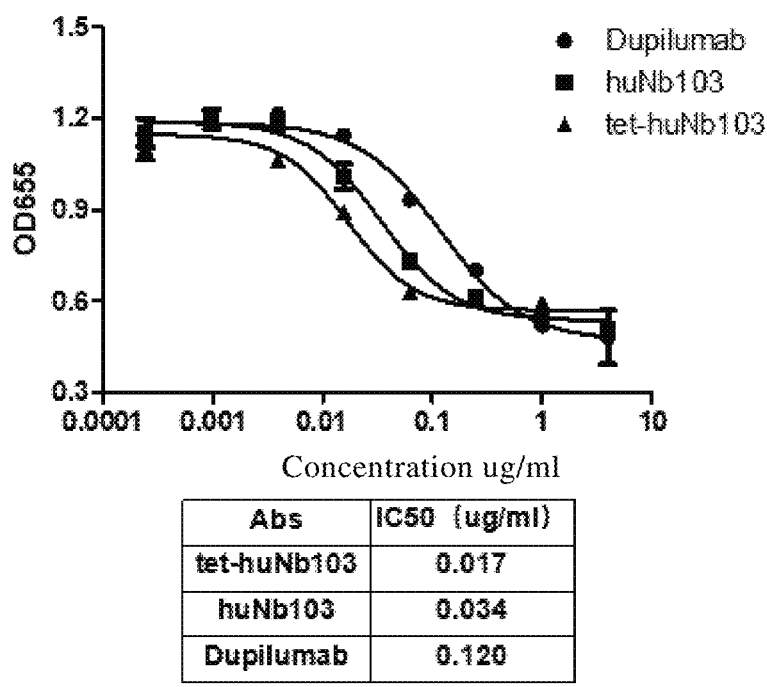
FIG. 15 shows the inhibitory effect of humanized tetravalent antibodies on the pSTAT6 signaling pathway in HEK-Blue™ IL-4/IL-13 cells induced by IL-13. Humanized tetravalent antibody can effectively inhibit the pSTAT6 signaling pathway of HEK-Blue™ IL-4/IL-13 cells induced by IL-13, with inhibitory activity IC$_{50tet-huNb103}$=0.017 ug/mL. Its activity is 2-3 times higher than that of human bivalent antibody (IC$_{50\ huNb103}$=0.034 ug/mL), and it is significantly superior to that of the control antibody on pSTAT6 signaling pathway (IC$_{50\ Dupilumab}$=0.120 ug/mL).

Similarly, humanized tetravalent antibodies significantly inhibit the pSTAT6 signaling pathway in HEK-Blue™ IL-4/IL-13 cells induced by IL-13. The concentration of IL-13 added during detection was 10 ng/mL, and the other steps were the same as above. The result is shown in FIG. 15: humanized tetravalent antibody can effectively inhibit the pSTAT6 signaling pathway of HEK-Blue™ IL-4/IL-13 cells induced by IL-13, and it inhibitory activity $IC_{50\ tet-huNb103}$ is 0.017 ug/mL. Its activity is twice as high as that of human bivalent antibody ($IC_{50\ huNb103}$=0.034 ug/mL) and is also significantly superior to the effect on the pSTAT6 signaling pathway in HEK-Blue™ IL-4/IL-13 cells of the control antibody ($IC_{50\ Dupilumab}$=0.120 ug/mL).

Example 11: The Efficacy of Humanized Tetravalent Antibody Verified by HIL4/hIL4Rα Transgenic Mouse OVA Model According to body weight, fifteen animals were randomly divided into 3 groups with 5 animals in each group. Group 1 was negative control group, group 2 was low dose group of the test article (5 mpK), and group 3 was high dose group of the test article (25 mpk). The animals in groups 1-3 underwent OVA sensitization and administration: 200 μg/mL OVA was prepared and injected intraperitoneally, 200 μL per animal. The sensitization was performed on days 0, 7 and 14. On days 21-25, 2% OVA was atomized for 30 min each time for 5 consecutive days. The test article was administered on days 20 and 23, and samples were collected for analysis on the next day after the stimulation operation on day 25.

Figure 16:
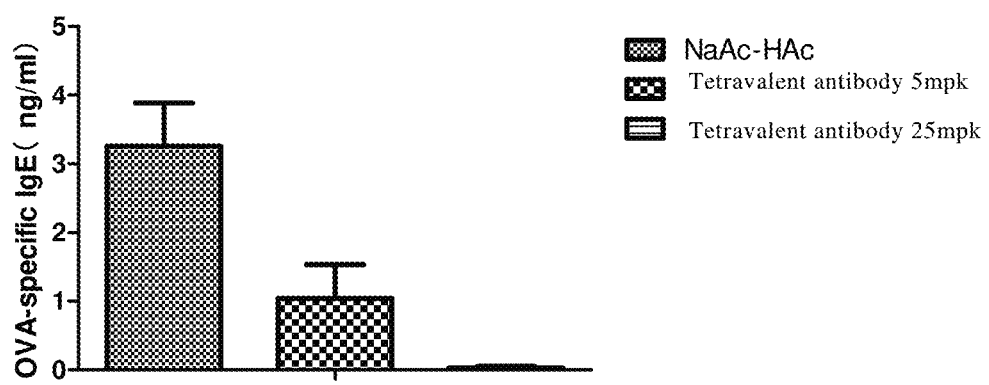
FIG. 16 shows the inhibition of OVA-specific IgE levels in serum in a transgenic mouse OVA model at two doses of 5 mpK and 25 mpK humanized tetravalent antibodies.

The results are shown in FIG. 16: both 5 mpK and 25 mpK doses of humanized tetravalent antibody can effectively inhibit the content of OVA-specific IgE in serum of transgenic mouse OVA models.

Figure 17A:
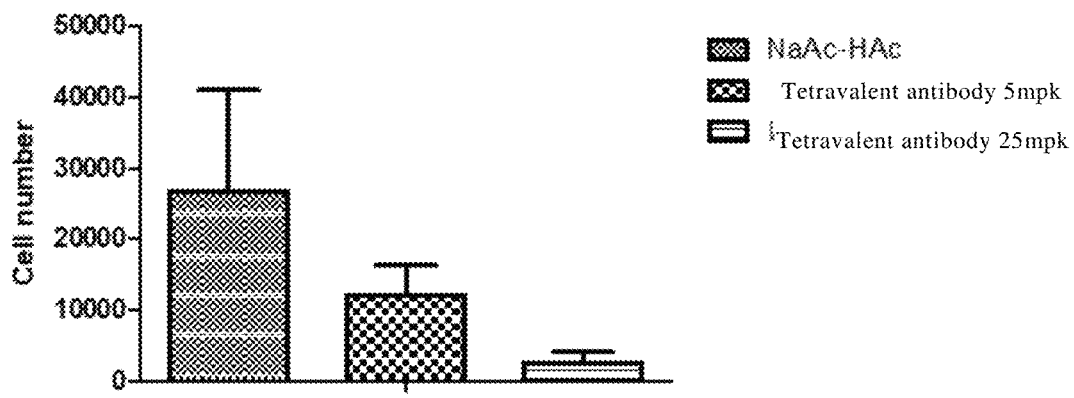
FIGS. 17A-17B show that humanized tetravalent antibodies at dose of 5 mpK and 25 mpK both can effectively reduce the number and ratio of pulmonary eosinophil.
Figure 17B:
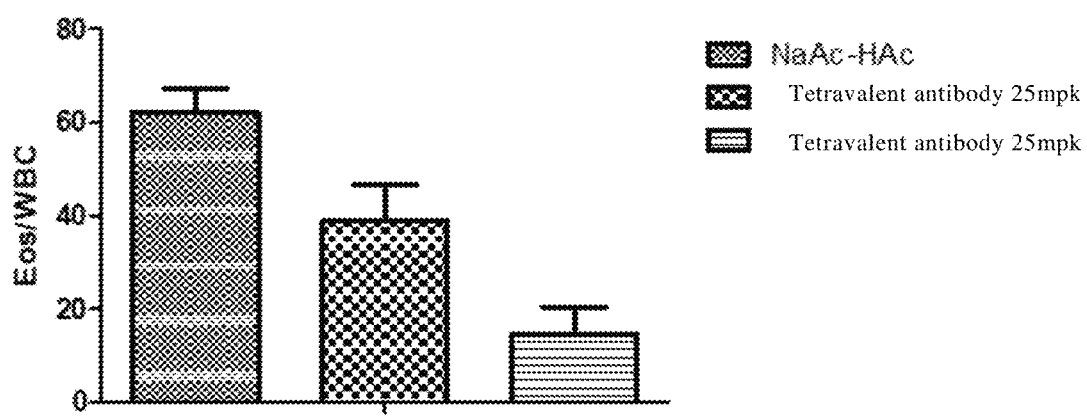

As shown in FIG. 17A and FIG. 17B, both 5 mpK and 25 mpK doses of humanized tetravalent antibody can effectively reduce the number and proportion of eosinophils in the lungs.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

```
Sequence information of the present invention:
                                      SEQ ID NO: 1
GSTSYRYCMA

SEQ ID NO: 2
IRPRSGRA

SEQ ID NO: 3
AASDNDGNCQDY

SEQ ID NO: 4
QVQLQESGGGSVQAGGSLRVSCAAS

SEQ ID NO: 5
WFRQAPGKEREAVAS

SEQ ID NO: 6
YYADSVKGRFTISLDNAKNTLYLQMNSLKPEDTAMY

SEQ ID NO: 7
YCWGKGTQVTVSS

SEQ ID NO: 8
QVQLQESGGGSVQAGGSLRVSCAASGSTSYRYCMA

WFRQAPGKEREAVASIRPRSGRAYYADSVKGRFTI

SLDNAKNTLYLQMNSLKPEDTAMYYCAASDNDGNC

QDYWGKGTQVTVSS

SEQ ID NO: 9
CAGGTGCAGCTGCAGGAGTCTGGGGGAGGCTCGGT

GCAGGCTGGAGGGTCTCTGAGAGTCTCCTGTGCAG

CCTCTGGATCCACCTCCTATAGATACTGTATGGCC

TGGTTCCGCCAGGCTCCAGGGAAGGAGCGCGAGGC

GGTCGCATCCATTCGCCCACGTAGTGGTAGGGCAT

ACTATGCCGACTCCGTGAAGGGCCGATTCACCATC

TCCCTAGACAACGCCAAGAACACGCTGTATCTGCA

AATGAACAGTCTGAAACCTGAGGACACTGCCATGT

ACTACTGTGCGGCCTCCGACAACGACGGTAATTGC

CAGGACTACTGGGGCAAAGGAACCCAGGTCACCGT

CTCCTCA

SEQ ID NO: 10
EVQLVESGGGLVQPGGSLRLSCAAS

SEQ ID NO: 11
WFRQAPGKGLEAVAS

SEQ ID NO: 12
YYADSVKGRFTISRDNSKNTLYLQMNSLRAEDTAVY
YC

SEQ ID NO: 13
WGKGTLVTVSS

SEQ ID NO: 14
EVQLVESGGGLVQPGGSLRLSCAASGSTSYRYCMA

WFRQAPGKGLEAVASIRPRSGRAYYADSVKGRFTI

SRDNSKNTLYLQMNSLRAEDTAVYYCAASDNDGNC

QDYWGKGTLVTVSS

SEQ ID NO: 15
CAGGTGCAGCTGCAGGAGAGCGGCGGCGGCCTGGT

GCAGCCCGGCGGCAGCCTGAGGCTGAGCTGCGCCG

CCAGCGGCAGCACCAGCTACAGGTACTGCATGGCC

TGGTTCAGGCAGGCCCCCGGCAAGGGCCTGGAGGC

CGTGGCCAGCATCAGGCCCAGGAGCGGCAGGGCCT

ACTACGCCGACAGCGTGAAGGGCAGGTTCACCATC

AGCAGGGACAACAGCAAGAACACCCTGTACCTGCA

GATGAACAGCCTGAGGGCCGAGGACACCGCCATGT

ACTACTGCGCCGCCAGCGACAACGACGGCAACTGC

CAGGACTACTGGGGCAAGGGCACCCTGGTGACCGT

GAGCAGC (SEQ ID NO: 16 = SEQ ID NO: 14 +
Fc fragment)
                                      SEQ ID NO: 16
EVQLVESGGGLVQPGGSLRLSCAASGSTSYRYCMA

WFRQAPGKGLEAVASIRPRSGRAYYADSVKGRFTI

SRDNSKNTLYLQMNSLRAEDTAVYYCAASDNDGNC
```

QDYWGKGTLVTVSSESKYGPPCPPCPAPEFLGGPS
VFLFPPKPKDTLMISRTPEVTCVVVDVSQEDPEVQ
FNWYVDGVEVHNAKTKPREEQFNSTYRVVSVLTVL
HQDWLNGKEYKCKVSNKGLPSSIEKTISKAKGQPR
EPQVYTLPPSEEMTKNQVSLTCLVKGFYPSDIAVE
WESNGQPENNYKTTPPVLDSDGSFFLYSRLTVDKS
RWQEGNVFSCSVMHEALHNHYTQKSLSLSLG

SEQ ID NO: 17
(nucleotide sequence encoding huNb103)
GAGGTGCAGCTGGTGGAGTCCGGCGGCGGCCTGGT
GCAGCCCGGCGGCTCCCTGAGGCTGTCCTGCGCCG
CCTCCGGCTCCACCTCCTACAGGTACTGCATGGCC
TGGTTCAGGCAGGCCCCCGGCAAGGGCCTGGAGGC
CGTGGCCTCCATCAGGCCCAGGTCCGGCAGGGCCT
ACTACGCCGACTCCGTGAAGGGCAGGTTCACCATC
TCCAGGGACAACTCCAAGAACACCCTGTACCTGCA
GATGAACTCCCTGAGGGCCGAGGACACCGCCGTGT
ACTACTGCGCCGCCTCCGACAACGACGGCAACTGC
CAGGACTACTGGGGCAAGGGCACCCTGGTGACCGT
GTCCTCCGAGTCCAAGTACGGCCCCCCCTGCCCCC
CCTGCCCCGCCCCGAGTTCCTGGGCGGCCCCTCC
GTGTTCCTGTTCCCCCCCAAGCCCAAGGACACCCT
GATGATCTCCAGGACCCCCGAGGTGACCTGCGTGG
TGGTGGACGTGTCCCAGGAGGACCCCGAGGTGCAG
TTCAACTGGTACGTGGACGGCGTGGAGGTGCACAA
CGCCAAGACCAAGCCCAGGGAGGAGCAGTTCAACT
CCACCTACAGGGTGGTGTCCGTGCTGACCGTGCTG
CACCAGGACTGGCTGAACGGCAAGGAGTACAAGTG
CAAGGTGTCCAACAAGGGCCTGCCCTCCTCCATCG
AGAAGACCATCTCCAAGGCCAAGGGCCAGCCCAGG
GAGCCCCAGGTGTACACCCTGCCCCCCTCCGAGGA
GATGACCAAGAACCAGGTGTCCCTGACCTGCCTGG
TGAAGGGCTTCTACCCCTCCGACATCGCCGTGGAG
TGGGAGTCCAACGGCCAGCCCGAGAACAACTACAA
GACCACCCCCCCCGTGCTGGACTCCGACGGCTCCT
TCTTCCTGTACTCCAGGCTGACCGTGGACAAGTCC
AGGTGGCAGGAGGGCAACGTGTTCTCCTGCTCCGT
GATGCACGAGGCCCTGCACAACCACTACACCCAGA
AGTCCCTGTCCCTGTCCCTGGGC SEQ ID NO: 18
<u>GGGGSGGGS</u>

(SEQ ID NO: 19 = SEQ ID NO: 14 +
SEQ ID NO: 18 + SEQ ID NO: 14 + Fcg
fragment)

SEQ ID NO: 19
EVQLVESGGGLVQPGGSLRLSCAASGSTSYRYCMA
WFRQAPGKGLEAVASIRPRSGRAYYADSVKGRFTI
SRDNSKNTLYLQMNSLRAEDTAVYYCAASDNDGNC
QDYWGKGTLVTVSS<u>GGGGSGGGS</u>EVQLVESGGGLV
QPGGSLRLSCAASGSTSYRYCMAWFRQAPGKGLEA
VASIRPRSGRAYYADSVKGRFTISRDNSKNTLYLQ
MNSLRAEDTAVYYCAASDNDGNCQDYWGKGTLVTV
SSESKYGPPCPPCPAPEFLGGPSVFLFPPKPKDTL
MISRTPEVTCVVVDVSQEDPEVQFNWYVDGVEVHN
AKTKPREEQFNSTYRVVSVLTVLHQDWLNGKEYKC
KVSNKGLPSSIEKTISKAKGQPREPQVYTLPPSEE
MTKNQVSLTCLVKGFYPSDIAVEWESNGQPENNYK
TTPPVLDSDGSFFLYSRLTVDKSRWQEGNVFSCSV
MHEALHNHYTQKSLSLSLG

SEQ ID NO: 20
GAAGTGCAGCTGGTGGAGTCGGAGGCGGCCTGGT
GCAGCCTGGAGGCTCTCTGAGACTGTCTTGTGCTG
CCTCTGGCAGCACATCTTACAGATACTGCATGGCC
TGGTTCAGACAGGCTCCTGGCAAGGGCCTGGAGGC
CGTGGCCTCTATCAGACCTAGATCTGGAAGGGCCT
ACTATGCTGACAGCGTGAAGGGCAGGTTCACAATC
TCTAGAGATAACTCTAAGAACACTCTGTACCTGCA
GATGAACTCTCTGAGAGCAGAGGATACCGCCGTGT
ACTACTGTGCCGCCAGCGATAACGATGGAAACTGT
CAGGATTATTGGGGCAAGGGAACACTGGTGACAGT
GTCTAGCGGCGGAGGCGGAAGCGGCGGCGGAAGCG
AGGTGCAGCTGGTGGAGTCCGGAGGCGGCCTGGTG
CAGCCAGGAGGCAGCCTGAGACTGAGCTGCGCCGC
CAGCGGCAGCACATCTTACAGGTACTGCATGGCCT
GGTTTAGGCAGGCTCCAGGAAAGGGCCTGGAGGCC
GTGGCCAGCATTAGACCCAGGAGCGGCAGAGCTTA
CTACGCCGACTCTGTGAAGGGCAGATTCACCATCA
GCAGAGATAACAGTAAGAACACCCTGTACCTGCAG
ATGAATAGCCTGAGAGCTGAGGATACCGCTGTGTA
TTACTGTGCTGCCTCTGACAACGACGGCAACTGTC
AGGATTACTGGGGAAAGGGCACACTGGTGACAGTG
TCTTCTGAGTCTAAGTACGGCCCACCTTGTCCTCC
TTGCCCTGCCCCCGAGTTTCTGGGAGGCCCATCTG
TGTTTCTGTTCCCTCCTAAGCCTAAGGACACACTG
ATGATTTCTAGAACACCTGAGGTGACTTGTGTGGT

```
GGTGGACGTGAGCCAGGAGGACCCTGAGGTGCAGT

TTAACTGGTACGTGGACGGCGTGGAGGTGCACAAC

GCCAAGACCAAGCCTAGAGAGGAGCAGTTCAACAG

CACCTACAGAGTGGTGAGCGTGCTGACCGTGCTGC

ACCAGGACTGGCTGAACGGCAAGGAGTACAAGTGC

AAGGTGAGCAACAAGGGACTGCCATCTAGCATCGA

GAAGACCATCTCTAAGGCCAAGGGCCAGCCAAGAG

AGCCACAGGTGTACACCCTGCCTCCTTCTGAGGAG
```

```
ATGACCAAGAACCAGGTGTCTCTGACCTGTCTGGT

GAAGGGCTTCTACCCTAGCGACATCGCCGTGGAGT

GGGAGTCCAACGGCCAGCCTGAGAACAACTACAAG

ACAACCCCACCTGTGCTGGATAGCGACGGCAGCTT

CTTTCTGTACAGCAGACTGACCGTGGATAAGTCTA

GGTGGCAGGAGGGAAACGTGTTTAGCTGTTCTGTG

ATGCACGAGGCCCTGCACAACCACTACACACAGAA

GAGCCTGTCTCTGAGCCTGGGC
```

---

The invention claimed is:

1. An anti-IL-4R single-domain antibody, which has a VHH chain comprising framework regions (FRs) and complementarity determining regions (CDRs), wherein the CDRs comprise CDR1 as shown in SEQ ID NO: 1, CDR2 as shown in SEQ ID NO: 2, and CDR3 as shown in SEQ ID NO: 3.

2. An antibody comprising one or more VHH chains of anti-IL-4R single-domain antibody, wherein the VHH chain comprises framework regions (FRs) and complementarity determining regions (CDRs), wherein the CDRs comprise CDR1 as shown in SEQ ID NO: 1, CDR2 as shown in SEQ ID NO: 2, and CDR3 as shown in SEQ ID NO: 3.

3. The anti-IL-4R single-domain antibody of claim 1, wherein the framework regions (FRs) comprise:
   (a) FR1 as shown in SEQ ID NO: 4, FR2 as shown in SEQ ID NO: 5, FR3 as shown in SEQ ID NO: 6, and FR4 as shown in SEQ ID NO: 7; or
   (b) FR1 as shown in SEQ ID NO: 10, FR2 as shown in SEQ ID NO: 11, FR3 as shown in SEQ ID NO: 12, and FR4 as shown in SEQ ID NO: 13.

4. The anti-IL-4R single-domain antibody of claim 1, wherein the single-domain antibody comprises one or more VHH chains whose amino acid sequence is as shown in SEQ ID NO: 8 or 14.

5. An anti-IL-4R single-domain antibody Fc fusion protein, wherein the fusion antibody has a structure as shown in Formula Ia or Ib from N-terminus to C-terminus:

A-L-B    (Ia);

B-L-A    (Ib);

wherein
   A is the anti-IL-4R single-domain antibody of claim 1;
   B is an Fc fragment of the IgG; and
   L is none or a flexible linker.

6. The fusion protein of claim 5, wherein the amino acid sequence of the Fc fragment is shown at positions 120-346 in SEQ ID NO: 16.

7. The fusion protein of claim 5, wherein the amino acid sequence of the fusion protein is as shown in SEQ ID NO: 16 or SEQ ID NO: 19.

8. A polynucleotide encoding the anti-IL-4R single-domain antibody of claim 1.

9. An expression vector containing the polynucleotide of claim 8.

10. An isolated host cell containing the expression vector of claim 9.

11. A method for producing an anti-IL-4R single-domain antibody or Fc fusion protein thereof, which comprises the steps of:
    (a) cultivating the host cell of claim 10 under a condition suitable for the production of a single-domain antibody or Fc fusion protein thereof, thereby obtaining a culture containing the anti-IL-4R single-domain antibody or Fc fusion protein thereof;
    (b) isolating or recovering the anti-IL-4R single-domain antibody or Fc fusion protein thereof from the culture; and
    (c) optionally, purifying and/or modifying the anti-TL-4R single-domain antibody or Fc fusion protein from step (b).

12. An immunoconjugate comprising:
    (a) the anti-IL-4R single-domain antibody of claim 1; and
    (b) a coupling moiety selected from the group consisting of a detectable label, a drug, a gold nanoparticle or nanorod, a magnetic nanoparticle, a viral coat protein or VLP, and a combination thereof.

13. The immunoconjugate of claim 12, wherein the detectable label is a radionuclide.

14. The immunoconjugate of claim 12, wherein the drug is selected from the group consisting of a toxin, cytokine, or enzyme.

15. A method of preparing the contrast agent to detect the IL-4R protein in vivo by using the immunoconjugate of claim 12.

16. A recombinant protein, which comprises:
    (i) the anti-IL-4R single-domain antibody of claim 1; and
    (ii) an optional tag sequence to aid expression and/or purification.

17. A method of preparing of a medicament, reagent, detection plate or kit;
    wherein the reagent, detection plate or kit is used for detecting IL-4R protein in a sample by using the anti-IL-4R single-domain antibody of claim 1;
    wherein the medicament is used for treating a disease or disorder associated with IL-4/IL-4R signaling transduction, wherein the disease or disorder is selected from the group consisting of asthma, atopic dermatitis, arthritis, allergic rhinitis or eczema.

18. An IL-4R protein detection reagent, which comprises:
    (i) the anti-IL-4R single-domain antibody of claim 1; and
    (ii) a detectologically acceptable carrier.

19. A kit for IL-4R protein detection, which comprises the detection reagent of claim 18, and a specification.

20. A pharmaceutical composition which comprises:
    (i) the anti-IL-4R single-domain antibody of claim 1; and
    (ii) a pharmaceutically acceptable carrier.

21. A method of treating a disease or disorder associated with IL-4/IL-4R signaling transduction, which comprises the step of administrating the anti-IL-4R single-domain antibody of claim 1 to a subject in need thereof, wherein the disease or disorder is selected from the group consisting of asthma, atopic dermatitis, arthritis, allergic rhinitis or eczema.

* * * * *